United States Patent
Lyden et al.

(10) Patent No.: US 11,406,530 B2
(45) Date of Patent: Aug. 9, 2022

(54) STAIRCASE METHOD FOR OPTIMIZED THERAPEUTIC HYPOTHERMIA

(71) Applicant: Cedars-Sinai Medical Center, Los Angeles, CA (US)

(72) Inventors: Patrick Lyden, Los Angeles, CA (US); Padmesh Rajput, Los Angeles, CA (US); Jessica Lamb, Los Angeles, CA (US); Mani Nezhad, Calabasas, CA (US); Konrad Schlick, West Hollywood, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1127 days.

(21) Appl. No.: 15/769,034

(22) PCT Filed: Nov. 4, 2016

(86) PCT No.: PCT/US2016/060524
§ 371 (c)(1),
(2) Date: Apr. 17, 2018

(87) PCT Pub. No.: WO2017/079553
PCT Pub. Date: May 11, 2017

(65) Prior Publication Data
US 2020/0237553 A1     Jul. 30, 2020

Related U.S. Application Data

(60) Provisional application No. 62/255,737, filed on Nov. 16, 2015, provisional application No. 62/250,811, filed on Nov. 4, 2015.

(51) Int. Cl.
*A61F 7/00*     (2006.01)
*G16H 40/63*     (2018.01)
(Continued)

(52) U.S. Cl.
CPC .............. *A61F 7/0097* (2013.01); *A61B 5/01* (2013.01); *A61F 7/10* (2013.01); *A61F 7/12* (2013.01);
(Continued)

(58) Field of Classification Search
CPC .................................... A61F 2007/0093–0096
See application file for complete search history.

(56) References Cited

U.S. PATENT DOCUMENTS

2002/0193855 A1* 12/2002 Dobak, III .............. A61P 43/00
                                                                                                                                            607/105
2007/0043409 A1* 2/2007 Brian, III .......... A61M 25/1002
                                                                                                                                            607/105

(Continued)

FOREIGN PATENT DOCUMENTS

WO        2017079553 A1     5/2017

OTHER PUBLICATIONS

International Search Report and Written Opinion of PCT Application No. PCT/US2016/060524, dated Jan. 10, 2017, 7 Pages.
(Continued)

*Primary Examiner* — Kaitlyn E Smith
(74) *Attorney, Agent, or Firm* — Nixon Peabody LLP; Linda B. Huber

(57) ABSTRACT

This invention relates to various methods and systems of using therapeutic hypothermia to treat medical conditions such as cardiac arrest, myocardial ischemia, cerebral ischemia, ischemia, stroke, traumatic brain or spinal cord injuries and hypoxic-ischemic injury.

18 Claims, 10 Drawing Sheets

(51) Int. Cl.
*A61B 5/01* (2006.01)
*A61F 7/10* (2006.01)
*A61F 7/12* (2006.01)
*A61M 19/00* (2006.01)

(52) U.S. Cl.
CPC ............ *A61M 19/00* (2013.01); *G16H 40/63* (2018.01); *A61F 2007/0002* (2013.01); *A61F 2007/0093* (2013.01); *A61M 2205/3606* (2013.01)

(56) References Cited

U.S. PATENT DOCUMENTS

2008/0132816 A1\* 6/2008 Kane ................. A61H 7/001
601/152
2013/0218196 A1 8/2013 Cheung

OTHER PUBLICATIONS

Nakamura et al., Influence of Rewarming Conditions after Hypothemia in Gerbils with Transient Forebrain Ischemia, 1999, J. Neurosurg, vol. 91, pp. 114-120.
Walter et al., Coupling of Cerebral Blood Flow and Oxygen Metabolism in Infant Pigs During Selective Brain Hypothemia, 2000, Journal of Cerebral Blood Flow and Metabolism, vol. 20, pp. 1215-1224.

\* cited by examiner

FIG. 3
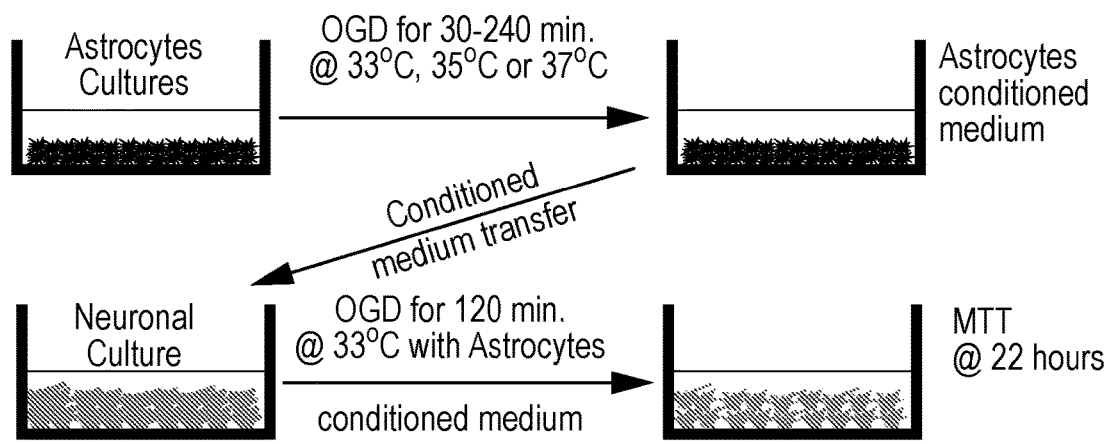
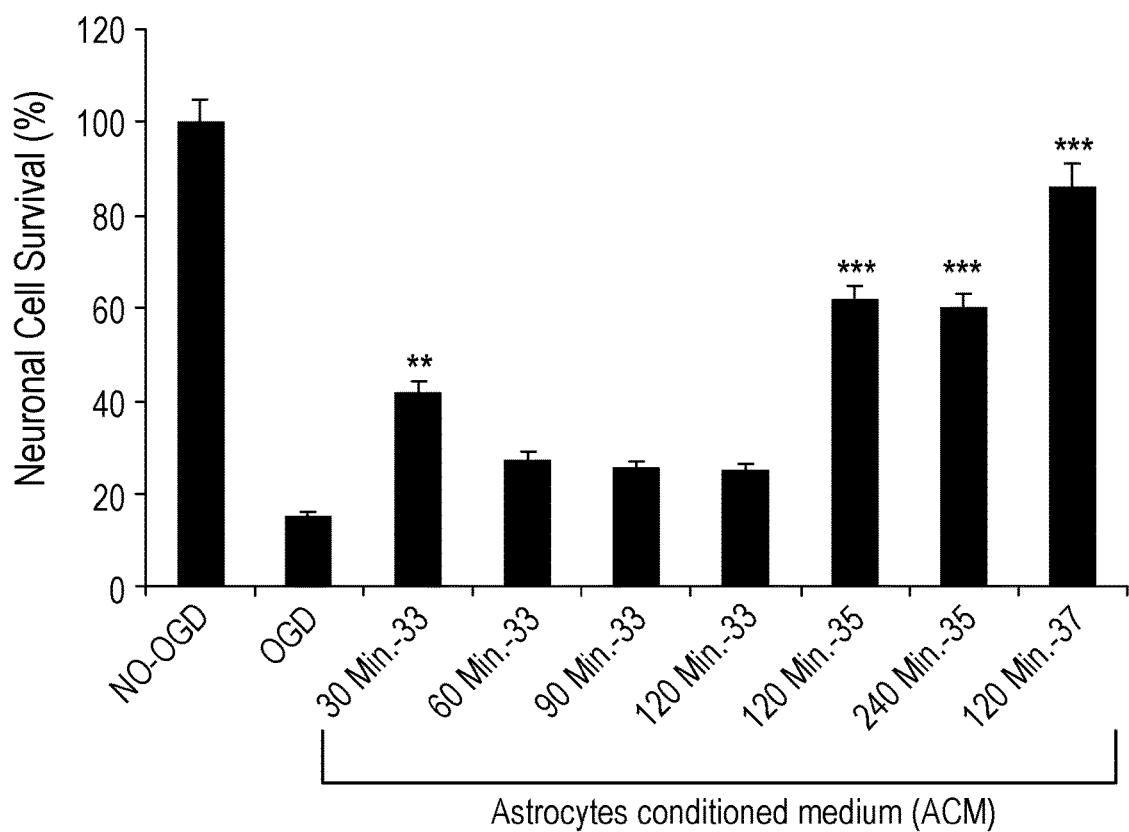

STAIRCASE METHOD FOR OPTIMIZED THERAPEUTIC HYPOTHERMIA

CROSS-REFERENCE TO RELATED APPLICATIONS

This application is a National Phase of International Application No. PCT/US2016/060524 filed Nov. 4, 2016, currently pending, which designated the U.S. and that International Application was published under PCT Article 21(2) in English, which also includes a claim of priority under 35 U.S.C. § 119(e) to U.S. provisional patent application No. 62/250,811 filed Nov. 4, 2015, and U.S. provisional patent application No. 62/255,737 filed Nov. 16, 2015, the entirety of which is hereby incorporated by reference.

FIELD OF THE INVENTION

The invention relates to methods and systems for treating a condition with therapeutic hypothermia (TH).

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Therapeutic hypothermia protects the brain after cardiac arrest and neonatal hypoxic-ischemic injury in patients. In animal models, therapeutic hypothermia protects brain and heart after cardiac arrest, myocardial ischemia, cerebral ischemia, ischemia, stroke, myocardial infarction, head trauma and a host of other insults. To date, therapeutic hypothermia has been administered at one target temperature (e.g. 33° C.) for a fixed duration (e.g. 24 hours), followed by a gradual "ramp" re-warm to normothermia. During the ramp re-warm, the core body temperature is tightly controlled to avoid over-shooting hyperthermia. The fixed ramp schedule arose from pilot studies in humans and animals in which rebound hyperthermia was observed, with concomitant elevations of intracranial pressure, unless the rewarm was carefully controlled during the ramp period. After achieving normothermia (e.g. 37.5° C.) the temperature is often regulated for a variable period of time to prevent later overshooting hyperthermia. The most common ramp re-warm rate is 0.8° C. per hour; thus, if a patient is to be rewarmed from 33° C. to 37.5° C. at 0.8° C. per hour, the ramp duration would be 5.6 hours. Conversely, some practitioners use fixed ramp duration of 12 hours, regardless of the starting and finishing temperatures.

In several clinical trials published to date (stroke, head trauma), therapeutic hypothermia has failed to show benefits commensurate with the benefit predicted from animal studies. The reasons for these failures are unclear. Without wishing to be bound by any particular theory, we postulate that traditional therapeutic hypothermia cooling/warming schedules failed in human clinical trials due to unappreciated aspects of cerebral pathophysiology. Therefore, there is still an unmet need of therapeutic hypothermia methods and systems.

SUMMARY OF THE INVENTION

The following embodiments and aspects thereof are described and illustrated in conjunction with systems, compositions and methods which are meant to be exemplary and illustrative, not limiting in scope.

Various embodiments of the present invention provide a method of treating, preventing, reducing the severity of and/or slowing the progression of a condition in a subject. In various embodiments, a body part of the subject has been affected by the condition for a time period T0. The method may consist of or may consist essentially of or may comprise: (a) reperfusing the affected body part for a time period TR; (b) implementing a first temperature transition C0 by changing the temperature of the subject's body and/or the affected body part to a first target temperature, and maintaining the temperature of the subject's body and/or the affected body part at the first target temperature for a time period of T1; (c) implementing a second temperature transition C1 by changing the temperature of the subject's body and/or the affected body part to a second target temperature, and maintaining the temperature of the subject's body and/or the affected body part at the second target temperature for a time period of T2; and (d) implementing a third temperature transition C2 by changing the temperature of the subject's body and/or the affected body part to a third target temperature, and maintaining the temperature of the subject's body and/or the affected body part at the third target temperature for a time period of T3, thereby treating, preventing, reducing the likelihood of having, reducing the severity of and/or slowing the progression of the condition in the subject. As readily appreciated by one of ordinary skill in the art, the method may further comprise additional steps of temperature transitions and maintenances, so as to achieve desirable treatment of the condition in the subject.

Various embodiments of the present invention provide a method of treating, preventing, reducing the severity of and/or slowing the progression of a condition in a subject. In various embodiments, a body part of the subject has been affected by the condition for a time period T0 and then reperfused for a time period TR. The method may consist of or may consist essentially of or may comprise: (a) implementing a first temperature transition C0 by changing the temperature of the subject's body and/or the affected body part to a first target temperature, and maintaining the temperature of the subject's body and/or the affected body part at the first target temperature for a time period of T1; (b) implementing a second temperature transition C1 by changing the temperature of the subject's body and/or the affected body part to a second target temperature, and maintaining the temperature of the subject's body and/or the affected body part at the second target temperature for a time period of T2; and (c) implementing a third temperature transition C2 by changing the temperature of the subject's body and/or the affected body part to a third target temperature, and maintaining the temperature of the subject's body and/or the affected body part at the third target temperature for a time period of T3, thereby treating, preventing, reducing the likelihood of having, reducing the severity of and/or slowing the progression of the condition in the subject. As readily appreciated by one of ordinary skill in the art, the method may further comprise additional steps of temperature transitions and maintenances, so as to achieve desirable treatment of the condition in the subject.

Various embodiments of the present invention provide a system. The system may consist of or may consist essentially of or may comprise: a temperature management module configured for changing and/or maintaining the temperature of a subject's body and/or body part; and a computer configured for operating the temperature management module to change and/or maintain the temperature of the subject's body and/or body part. In various embodiments, the system further comprises a detection module configured for detecting biomarkers in the subject's body and/or body part, wherein the computer is configured for operating the detection module to detect biomarkers in the subject's body and/or body part.

Various embodiments of present invention provide a computer. The computer comprises: a memory configured for storing one or more programs; and one and more processors configured for executing the one or more programs, wherein the one or more programs comprise instructions for operating a temperature management module to change and/or maintain the temperature of a subject's body and/or body part. In various embodiments, the one or more programs further comprise instructions for operating a detection module to detect biomarkers in the subject's body and/or body part.

Various embodiments of present invention provide a non-transitory computer-readable storage medium. The non-transitory computer-readable storage medium is configured for storing one or more programs, the one or more programs are configured for execution by one or more processors of a computer, and the one or more programs comprise instructions for operating a system and/or modules thereof to change and/or maintain the temperature of a subject's body and/or body part. In various embodiments, the one or more programs comprise instructions for operating the system and/or modules thereof to control the temperature of the subject's body and/or body part. In various embodiments, the one or more programs further comprise instructions for operating the system and/or modules thereof to detect biomarkers in the subject's body and/or body part.

Various methods, systems, computers and non-transitory computer-readable storage media of the present invention find utility in the treatment of various conditions, including but not limited to various forms of hypoxemia, hypoxia, ischemia, myocardial ischemia, cerebral ischemia, cardiac arrest, stroke, ischemic stroke, hemorrhagic stroke, transient ischemic attack, traumatic brain injury, traumatic spinal cord injury, hypoxic-ischemic injury, or hypoxic-ischemic encephalopathy, perinatal asphyxia, or a combination thereof.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 2A and FIG. 2B: No Delay: hypothermia (33 or 35) began at the end of 2 h OGD and continued for 2 h, 4 h or 24 h. FIG. 2C and FIG. 2D: 90 min delay between OGD end and start cooling. Using the MTT viability assay (FIG. 2A and FIG. 2C), hypothermia protected neurons after no delay (FIG. 2A, all durations). After 90 min (FIG. 2C) only duration 6 or 24 h at 33° C. was effective. Using LDH release (FIG. 2B and FIG. 2D), no delay hypothermia at 33° C. or 35° C. protected after all durations. After 90 min delay (FIG. 2D), 33° C. hypothermia shows protection at durations of 6 or 24 h *$p<0.05$, $p<0.01$,* $p<0.001$ comparing 33° C. to 35° C. Regardless of depth or duration, all hypothermia was superior to normothermia (FIG. 2A and FIG. 2B) after no delay (ANOVA, Dunnett's, ###$p<0.001$, φ $p<0.05$, φφφ $p<0.001$). *–33° C. vs 35° C., #–37° C. vs 33° C. and φ–37° C. vs 35° C.

FIG. 3 depicts, in accordance with various embodiments of the invention, protective effect of hypothermia mediated by astrocytes conditioned media. Astrocytes conditioned media was collected after subjecting astrocytes cultures to OGD ranging from 30-240 mins at 33, 35 and 37° C. ACM was added to primary neurons and followed by 2 hours OGD at 37° C. The cell viability of neurons was assessed by MTT assay 24 hours later. ACM from astrocytes subjected to 30 mins OGD at 33° C. were significantly protective,  $p<0.01$, whereas 60-120 min was not significant. However the ACM from 120 min and 240 mins showed significant neuroprotection, *$p<0.001$.

(FIG. 6B).

DETAILED DESCRIPTION OF THE INVENTION

Figure 1:
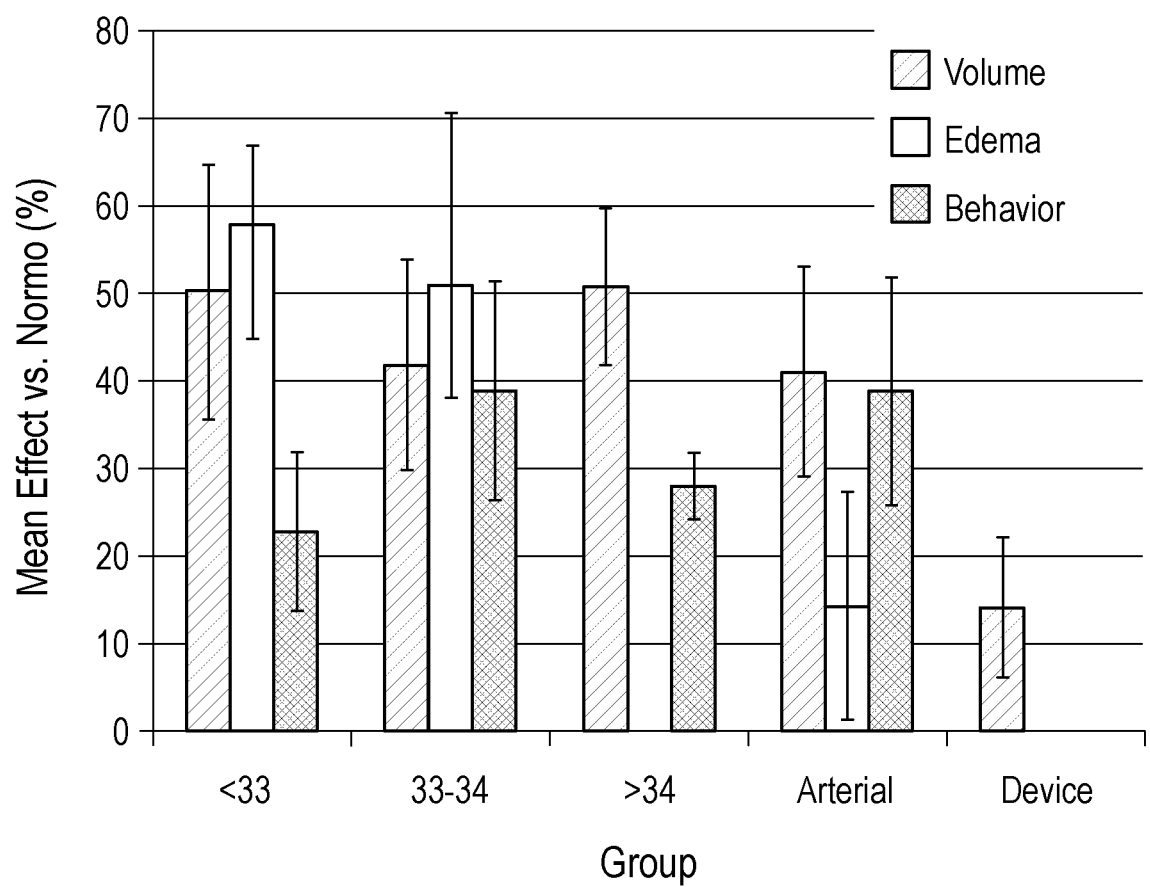
FIG. 1 depicts, in accordance with various embodiments of the invention, updated meta-analysis of preclinical studies of therapeutic hypothermia (TH). The y-axis shows the mean±SD treatment effect size vs. normothermia for all papers included. The x-axis groups all trials by target temperature for surface cooling; intra-arterial saline infusions; or as cranial cooling device. All depths of TH significantly improved stroke volume (blue bars) compared to normothermia irrespective of modality. Effect sizes ranged from 30 to over 60%. The effects on neurobehavioral scores in using variety of scoring methods and behavioral tasks also showed benefit. Intracarotid saline was not significantly different than whole body cooling. There were many fewer studies of the effect of TH on cerebral edema (red bars): all levels of TH were superior to normothermia. Onset to treatment, however, was longer in the 4 studies of intracarotid saline, mean±SD 75±90 min (NS by ANOVA).
Figure 2A:
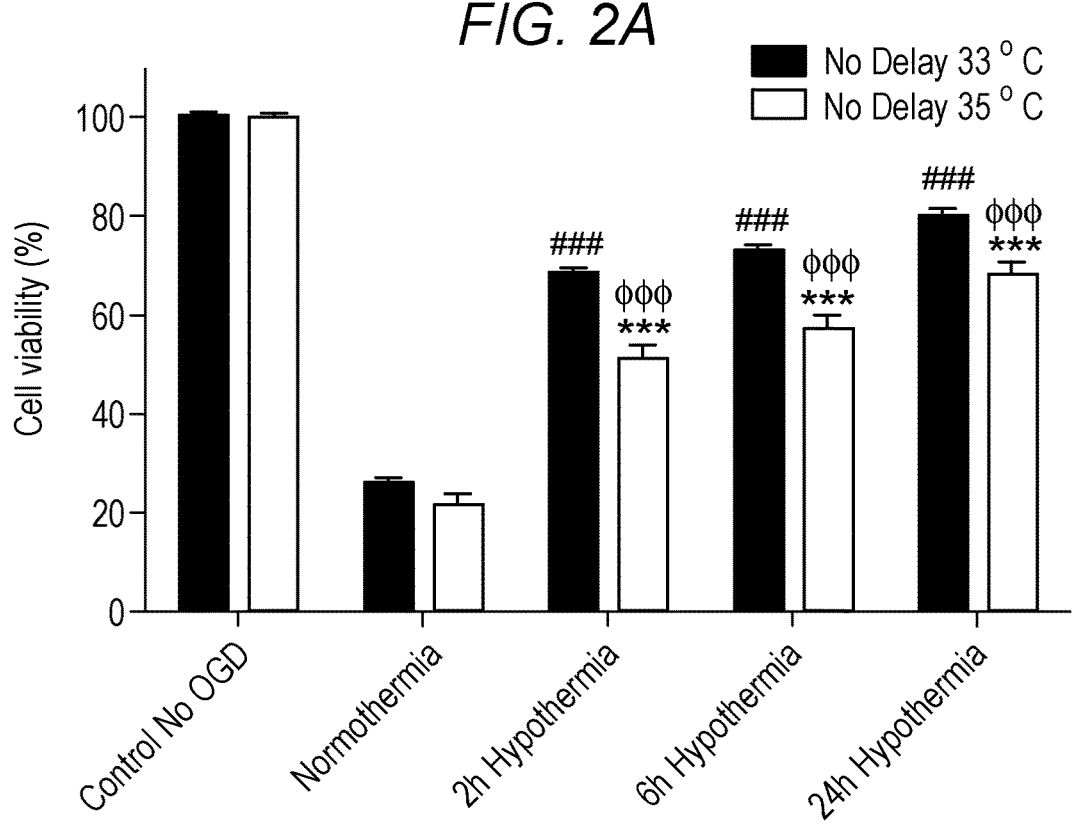
FIG. 2A-FIG. 2D depict, in accordance with various embodiments of the invention, effects of varying depth, duration and delay in neuronal oxygen-glucose deprivation (OGD).
Figure 2B:
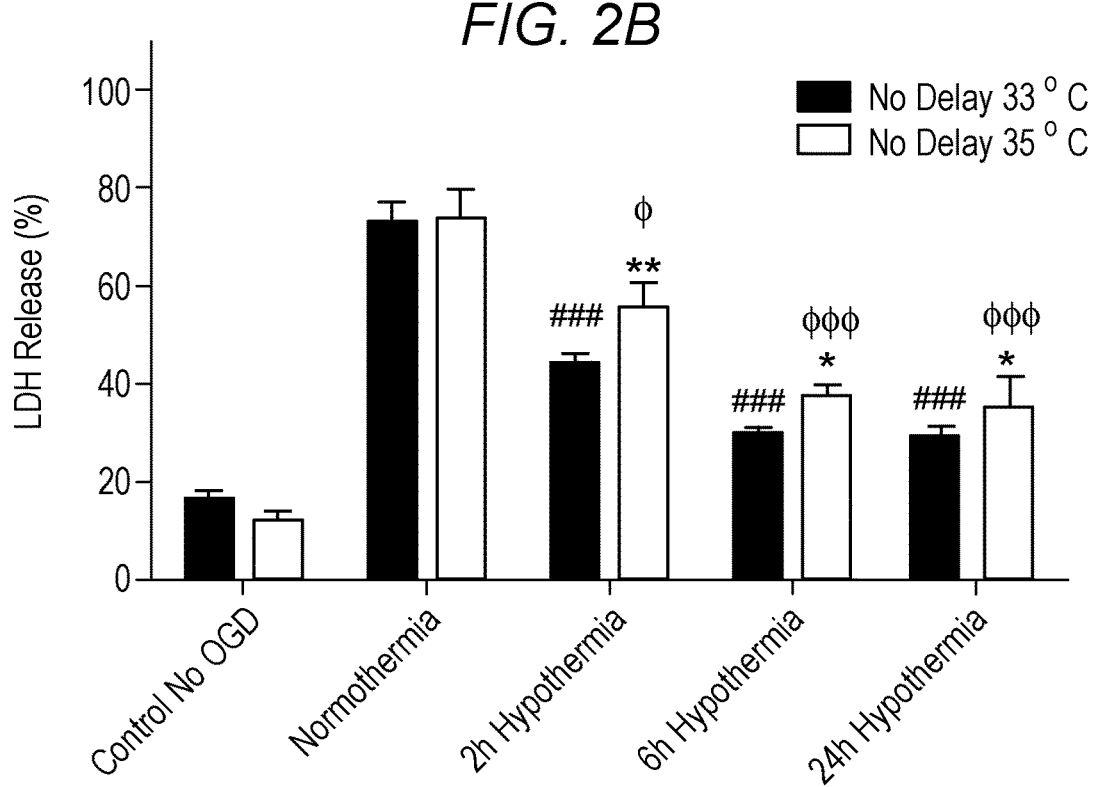
Figure 2C:
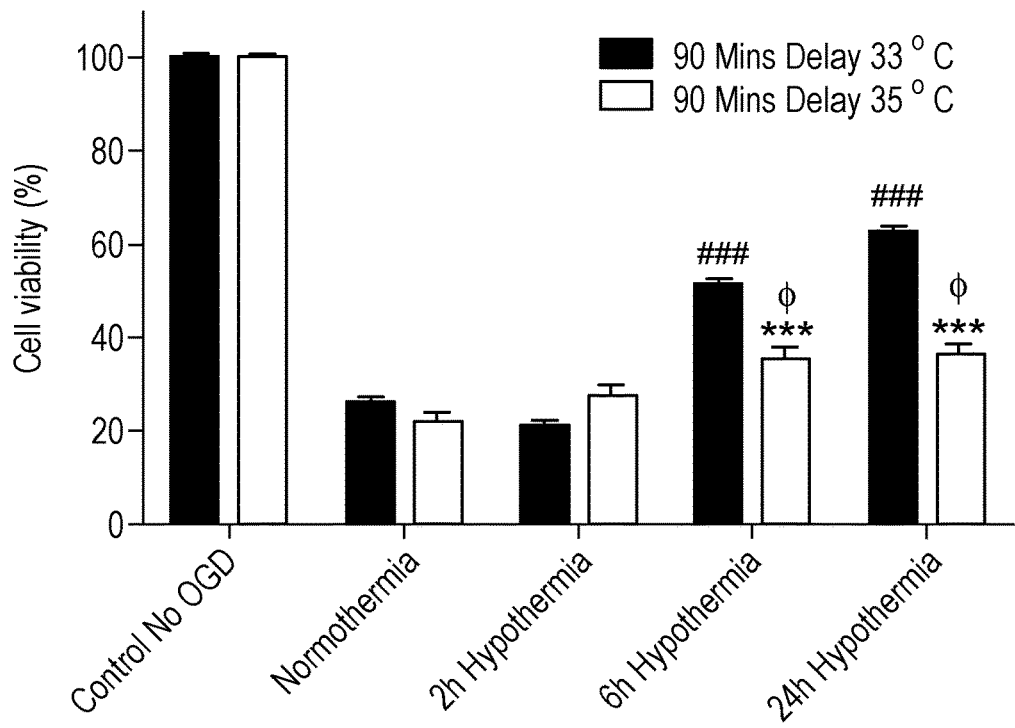
Figure 2D:
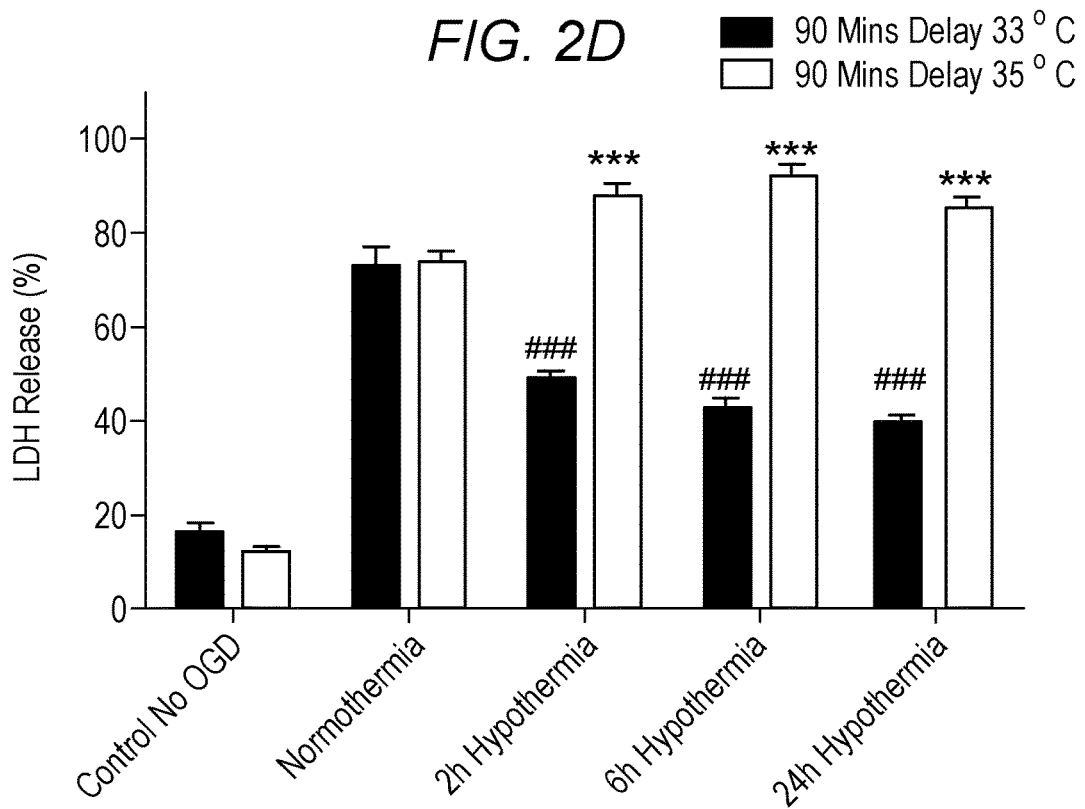

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22nd ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3rd ed., revised ed., J. Wiley & Sons (New York, N.Y. 2006); Smith, *March's Advanced Organic Chemistry Reactions, Mechanisms and Structure* 7th ed., J. Wiley & Sons (New York, N.Y. 2013); Singleton, *Dictionary of DNA and Genome Technology* 3rd ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective"

if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of ischemia or hemorrhage, delay or slowing of ischemia or hemorrhage, and amelioration or palliation of symptoms associated with ischemia or hemorrhage.

"Disorders", "diseases", "conditions" and "disease conditions," as used herein may include, but are in no way limited to any form of cardiac arrest, myocardial ischemia, cerebral ischemia, ischemia, stroke, ischemic stroke, hemorrhagic stroke, subarachnoid hemorrhage, head trauma, spinal cord injury, traumatic central nervous system (CNS) injuries, traumatic brain or spinal cord injury, infant hypoxic-ischemic injury, neonatal encephalopathy, perinatal hypoxia-ischemia, hypoxic ischemic encephalopathy, and birth asphyxia, and their related conditions, diseases or disorders.

The term "sample" or "biological sample" as used herein denotes a sample taken or isolated from a biological organism. Exemplary biological samples include, but are not limited to, cheek swab; mucus; whole blood, blood, serum; plasma; urine; saliva; semen; lymph; fecal extract; sputum; other body fluid or biofluid; cell sample; and tissue sample etc. The term also includes a mixture of the above-mentioned samples. The term "sample" also includes untreated or pretreated (or pre-processed) biological samples. In some embodiments, a sample can comprise one or more cells from the subject.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Overshoot" or "overshooting" as used herein refers to an act of going past or beyond a target value. Examples of target value include but are not limited to target temperature, target time or combinations thereof.

"Ramp" or "Ramp re-warm" as used herein refers to gradual rewarming of the subject in a controlled manner so as to avoid "overshoot".

"Target-depth" as used herein refers to the intended temperature for therapeutic hypothermia.

"Depth-delay-duration" as used herein refers to the relationship amongst the target depth temperature, the delay from onset of ischemia to the beginning of cooling, and the duration of cooling.

A subject can be one who has been previously diagnosed with or identified as suffering from or having a condition in need of treatment (e.g., cardiac arrest, myocardial ischemia, cerebral ischemia, ischemia, stroke, traumatic brain or spinal cord injuries, and hypoxic-ischemic injury) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. For example, a subject can be one who exhibits one or more symptoms for a condition or one or more complications related to the condition or a subject who does not exhibit symptoms. A "subject in need" of diagnosis or treatment for a particular condition can be a subject suspected of having that condition, diagnosed as having that condition, already treated or being treated for that condition, not treated for that condition, or at risk of developing that condition.

The term "statistically significant" or "significantly" refers to statistical evidence that there is a difference. It is defined as the probability of making a decision to reject the null hypothesis when the null hypothesis is actually true. The decision is often made using the p-value.

Therapeutic hypothermia is used in patients suffering stroke, cardiac arrest, head trauma, subarachnoid hemorrhage, and in infants after hypoxic-ischemic injury. Globally these insults occur in millions of patients every year, but only hundreds of thousands arrive in medical centers in time to be treated. However, in several clinical trials published to date (stroke, head trauma), therapeutic hypothermia has failed to show benefits commensurate with the benefit predicted from animal studies. The reasons for these failures are unclear.

Without wishing to be bound by any particular theory, we postulate that traditional therapeutic hypothermia cooling/warming schedules failed in human clinical trials due to unappreciated aspects of cerebral pathophysiology. Recently some key aspects of brain pathophysiology have become clear. For example, it is recognized that the brain consists of multiple cell types working together in an arrangement call the neurovascular unit (NVU). The cell types comprising the NVU include neurons, astrocytes, endothelial cells, pericytes, oligodendroglia, and microglia. Very recently considerable data has emerged to show that different elements of the NVU behave quite differently during injury. For example, we showed that astrocytes tolerate substrate deprivation (removal of oxygen and glucose) up to 5 times longer than neurons. Endothelial cells are intermediate.

Moreover, we recently discovered that astrocytes subjected to substrate deprivation (pre-conditioning) produce a transferable, heat-labile, trypsin-digestible factor that protects neurons from similar substrate deprivation. We are the first to show that the protective effect of astrocytes is transferable (paracrine). Astrocyte protection of neurons can be blocked, however, by incubating the cells at 33° C. while incubation at 35° C. partially inhibits the protective effect. Thus, in the human stroke or head trauma patient, single-target hypothermia for a fixed duration, followed by a fixed ramp re-warm, could inhibit considerable neuroprotective activity in the neurovascular unit. The outcome, despite robust hypothermic protection of neurons, could be unfavorable if the overall net effect from therapeutic hypothermia would be inhibitory.

Furthermore, we have known that the depth of target temperature drop and duration of therapeutic hypothermia must be adjusted based on the delay time from injury onset to therapy initiation. Our own data supports the existence of a delay-depth-duration relationship in all 3 main elements of the neurovascular unit: neurons, astrocytes, and endothelial cells, but on very different time scales.

Considering these observations, the inventors provide therapeutic hypothermia methods that are alternative to the traditional approach. Also, therapeutic hypothermia is applied by machines that cool patients. The machine is attached to a sensor on the patient that measures body temperature, and then cools the patient via surface pads, cooling blankets, cooling helmets, internal catheters, ice packs, intra-arterial infusion of cold saline and/or ice water lavage. In some embodiments, intra-arterial infusion of cold saline may be used for therapeutic hypothermia. The machine contains an internal algorithm or program to control cooling. Thus, the inventors' treatment methods as disclosed herein may be implemented as algorithms or programs installed in such machines, so that the cooling occurs according to the inventors' treatment methods, rather than the traditional approach.

Methods of Therapeutic Hypothermia

Various embodiments of the present invention provide a method of treating, preventing, reducing the likelihood of having, reducing the severity of and/or slowing the progression of a condition in a subject. In various embodiments, a body part of the subject has been affected by the condition for a time period T0. The method comprises: (a) reperfusing the affected body part for a time period TR; (b) implementing a first temperature transition C0 by changing the temperature of the subject's body and/or the affected body part to a first target temperature, and maintaining the temperature of the subject's body and/or the affected body part at the first target temperature for a time period of T1; (c) implementing a second temperature transition C1 by changing the temperature of the subject's body and/or the affected body part to a second target temperature, and maintaining the temperature of the subject's body and/or the affected body part at the second target temperature for a time period of T2; and (d) implementing a third temperature transition C2 by changing the temperature of the subject's body and/or the affected body part to a third target temperature, and maintaining the temperature of the subject's body and/or the affected body part at the third target temperature for a time period of T3, thereby treating, preventing, reducing the likelihood of having, reducing the severity of and/or slowing the progression of the condition in the subject.

Various embodiments of the present invention provide a method of treating, preventing, reducing the severity of and/or slowing the progression of a condition in a subject. In various embodiments, a body part of the subject has been affected by the condition for a time period T0 and then reperfused for a time period TR. The method comprises: (a) implementing a first temperature transition C0 by changing the temperature of the subject's body and/or the affected body part to a first target temperature, and maintaining the temperature of the subject's body and/or the affected body part at the first target temperature for a time period of T1; (b) implementing a second temperature transition C1 by changing the temperature of the subject's body and/or the affected body part to a second target temperature, and maintaining the temperature of the subject's body and/or the affected body part at the second target temperature for a time period of T2; and (c) implementing a third temperature transition C2 by changing the temperature of the subject's body and/or the affected body part to a third target temperature, and maintaining the temperature of the subject's body and/or the affected body part at the third target temperature for a time period of T3, thereby treating, preventing, reducing the likelihood of having, reducing the severity of and/or slowing the progression of the condition in the subject.

In various embodiments, the condition is hypoxemia, hypoxia, ischemia, myocardial ischemia, cerebral ischemia, cardiac arrest, stroke, ischemic stroke, hemorrhagic stroke, transient ischemic attack, traumatic brain injury, traumatic spinal cord injury, hypoxic-ischemic injury, or hypoxic-ischemic encephalopathy, perinatal asphyxia, or a combination thereof. In various embodiments, the affected body part is heart, brain, or spinal cord, or a combination thereof. In various embodiments, the subject is a human, an infant, a child, a teenager, or an adult.

As readily appreciated by one of ordinary skill in the art, the method may further comprise additional steps of temperature transitions and maintenances, so as to achieve desirable treatment of the condition in the subject. For example, in various embodiments, the method further comprises: (e) implementing a fourth temperature transition C3 by changing the temperature of the subject's body and/or the affected body part to a fourth target temperature, and maintaining the temperature of the subject's body and/or the affected body part at the fourth target temperature for a time period of T4. For example, in various embodiments, the method further comprises: (f) implementing a fifth temperature transition C4 by changing the temperature of the subject's body and/or the affected body part to a fifth target temperature, and maintaining the temperature of the subject's body and/or the affected body part at the fifth target temperature for a time period of T5.

In various embodiments, T0 is up to about 0-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, or 290-300 minutes. In some embodiments, T0 is up to about 200 minutes. In various embodiments, T0 is about 0-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, or 290-300 minutes.

In various embodiments, TR is up to about 0-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, or 290-300 minutes. In some embodiments, TR is up to about 200 minutes. In various embodiments, TR is about 0-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, or 290-300 minutes.

In various embodiments, T1 is up to about 0-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, or 290-300 minutes. In various embodiments, T1 is up to about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 hour. In various embodiments, T1 is up to about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 days. In some embodiments, T1 is up to about 14 days. In various embodiments, T1 is about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 days.

In various embodiments, T2 is up to about 0-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, or 290-300 minutes. In various embodiments, T2 is up to about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 hour. In various embodiments, T2 is up to about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 days. In some embodiments, T2 is up to about 14 days. In various embodiments, T2 is about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 days.

In various embodiments, T3 is up to about 0-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, or 290-300 minutes. In various embodiments, T3 is up to about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 hour. In various embodiments, T3 is up to about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 days. In some embodiments, T3 is up to about 14 days. In various embodiments, T3 is about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 days.

In various embodiments, T4 is up to about 0-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, or 290-300 minutes. In various embodiments, T4 is up to about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 hour. In various embodiments, T4 is up to about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 days. In some embodiments, T4 is up to about 14 days. In various embodiments, T4 is about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 days.

In various embodiments, T5 is up to about 0-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, or 290-300 minutes. In various embodiments, T5 is up to about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 hour. In various embodiments, T5 is up to about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 days. In some embodiments, T5 is up to about 14 days. In various embodiments, T5 is about 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, or 23-24 days.

In various embodiments, the first target temperature is lower than the temperature of the subject's body and/or the affected body part. In some embodiments, the first target temperature is about 27, 28, 29, 30, 31, 32, 33, 34, 35, or 36° C. In certain embodiments, the first target temperature is about 33° C.

In various embodiments, the second target temperature is higher than the first target temperature. In some embodiments, the second target temperature is about 32, 33, 34, 35, 36, 37, or 38° C. In certain embodiments, the second target temperature is about 35° C.

In various embodiments, the third target temperature is higher than the second target temperature. In some embodiments, the third target temperature is about 34, 35, 36, 37, 38, 39, or 40° C. In certain embodiments, the third target temperature is about 37° C.

In various embodiments, the fourth target temperature is lower than the third target temperature. In some embodiments, the fourth target temperature is about 27, 28, 29, 30, 31, 32, 33, 34, 35, or 36° C. In certain embodiments, the fourth target temperature is about 33° C.

In various embodiments, the fifth target temperature is higher than the fourth target temperature. In some embodiments, the fifth target temperature is about 34, 35, 36, 37, 38, 39, or 40° C. In certain embodiments, the fifth target temperature is about 37° C.

In some embodiments, the first target temperature is about 33° C., the second target temperature is about 35° C., and the third target temperature is about 37° C. In some embodiments, the first target temperature is about 33° C., the second target temperature is about 35° C., the third target temperature is about 37° C., the fourth target temperature is about 33° C., and the fifth target temperature is about 37° C.

In various embodiments, one, or more, or all of the temperature transitions (e.g., C0, C1, C2, C3, and C4) are accomplished rapidly. In accordance with the present invention, a variety of cooling methods may be used to implement one, or more, or all of the temperature transitions (e.g., C0, C1, C2, C3, and C4). Examples of these cooling methods include but are not limited to: surface cooling with ice packs, surface cooling with blankets, wraps, intra-arterial infusion of cold saline, surface heat-exchange devices, surface cooling with helmets, caps or suites, internal cooling using catheter-based technologies, and internal cooling using infusion of cold fluids.

In some embodiments, one, or more, or all of the temperature transitions (e.g., C0, C1, C2, C3, and C4) are accomplished within about 1-5, 5-10, 10-15, 15-20, 20-25, 25-30, 30-35, 35-40, 40-45, 45-50, 50-55, or 55-60 minutes. In some embodiments, one, or more, or all of the temperature transitions (e.g., C0, C1, C2, C3, and C4) are accomplished within about 60-65, 65-70, 70-75, 75-80, 80-85, 85-90, 90-95, 95-100, 100-105, 105-110, 110-115, or 115-120 minutes.

In various embodiments, C0 is accomplished within about 1-5, 5-10, 10-15, 15-20, 20-25, 25-30, 30-35, 35-40, 40-45, 45-50, 50-55, or 55-60 minutes. In various embodiments, C1 is accomplished within about 1-5, 5-10, 10-15, 15-20, 20-25, 25-30, 30-35, 35-40, 40-45, 45-50, 50-55, or 55-60 minutes. In various embodiments, C2 is accomplished within about 1-5, 5-10, 10-15, 15-20, 20-25, 25-30, 30-35, 35-40, 40-45, 45-50, 50-55, or 55-60 minutes. In various embodiments, C3 is accomplished within about 1-5, 5-10, 10-15, 15-20, 20-25, 25-30, 30-35, 35-40, 40-45, 45-50, 50-55, or 55-60 minutes. In various embodiments, C4 is accomplished within about 1-5, 5-10, 10-15, 15-20, 20-25, 25-30, 30-35, 35-40, 40-45, 45-50, 50-55, or 55-60 minutes.

In various embodiments, C0 is initiated upon encountering a subject with a condition that qualifies the subject as a candidate for therapeutic hypothermia. In various embodiments, C1 is initiated upon detecting a second biomarker in the subject's body and/or the affected body part. In various embodiments, C2 is initiated upon detecting a third biomarker in the subject's body and/or the affected body part. In various embodiments, C3 is initiated upon detecting a fourth biomarker in the subject's body and/or the affected body part. In various embodiments, C4 is initiated upon detecting a fifth biomarker in the subject's body and/or the affected body part. The first, second, third, fourth, and fifth biomarkers may be the same biomarker or different biomarkers. Examples of biomarkers include cold-shock proteins, inflammatory markers, cytoskeletal markers, chemokines, metabolites, RBMP3, CIRB3, PI3K, CREB, ERK1/2, and PKC-α.

In various embodiments, a method as disclosed applies the equation $(T1+T2)=xT0$ to determine parameter values. In various embodiments, a method as disclosed applies the equation $(T1+T2)=xT0+yTR$ to determine parameter values. In various embodiments, a method as disclosed applies the equation total time $xT0+yTR=fT1+(1-f)T2$ to determine parameter values. In certain embodiments, x is 1, y is 2, and f is ½.

In some embodiments, x is an integer, a negative integer, a positive integer, a non-negative integer, a non-positive integer, or zero. In some embodiments, x is 0, 1, 2, 3, 4, or 5, or another integer. In some embodiments, y is an integer, a negative integer, a positive integer, a non-negative integer, a non-positive integer, or zero. In some embodiments, y is 0, 1, 2, 3, 4, or 5, or another integer. In some embodiments, x and y comply with a numeric sequence, including but not limited to a simple sequence (e.g., 1-2-3-4-5 . . . ), an exponential sequence (e.g., 1-4-9-16-25 . . . ), and a Fibonacci sequence (e.g., 1-2-3-5-8 . . . ).

In various embodiments, f has a non-negative value, a positive value or zero. In various embodiments, f is a fraction, simple fraction, complex fraction, compound fraction, or mixed number. In various embodiments, f is a common, vulgar, or simple fraction that consists an integer numerator, displayed above a line (or before a slash), and a non-zero integer denominator, displayed below (or after) that line. In various embodiments, f is 0, ½, ⅓, ⅔, ¼, ¾, ⅕, ⅖, ⅗, ⅘, ⅙, ⅚, 1/7, 2/7, 3/7, 4/7, 5/7, 6/7, ⅛, ⅜, ⅝, ⅞, 1/9, 2/9, 3/9, 4/9, 5/9, 6/9, 7/9, 8/9, 1/10, 3/10, 7/10, 9/10, or 1.

Treatment Systems, Computers, and Programs

The present invention also provides various systems, computers, non-transitory computer-readable storage media for administering various methods of therapeutic hypothermia described herein.

Various embodiments of the present invention provide a system. The system comprises: a temperature management module configured for changing and/or maintaining the temperature of a subject's body and/or body part; and a computer configured for operating the temperature management module to change and/or maintain the temperature of the subject's body and/or body part.

In various embodiments, the system further comprises a detection module configured for detecting biomarkers in the subject's body and/or body part, wherein the computer is configured for operating the detection module to detect biomarkers in the subject's body and/or body part.

In various embodiments, the temperature management module comprises one or more temperature sensors configured for measuring the temperature of the subject's body and/or body part. In various embodiments, the temperature management module comprises a cooling catheter, cooling blanket, ice pack, iced lavage, transnasal cooling cannula, cooling helmet, cooling cap, cooling wrap, gel pad, or extracorporeal blood cooling machine, or a combination thereof.

In various embodiments, the computer comprises: a memory configured for storing one or more programs; and one and more processors configured for executing the one or more programs, wherein the one or more programs comprise instructions for operating the system and/or various modules thereof. In some embodiments, the one or more programs comprise instructions for operating a temperature management module configured for changing and/or maintaining the temperature of the subject's body and/or body part. In some embodiments, the one or more programs comprise instructions for operating a detection module configured for detecting biomarkers in the subject's body and/or body part.

Various embodiments of present invention provide a method of treating, preventing, reducing the likelihood of having, reducing the severity of and/or slowing the progression of a condition in a subject. The method comprises: providing a system as disclosed herein; operating the system and/or various modules thereof to change and/or maintain the temperature of the subject's body and/or body part, thereby treating, preventing, reducing the likelihood of having, reducing the severity of and/or slowing the progression of the condition in the subject. In various embodiments, the method comprises operating the system and/or various modules thereof to control the temperature of the subject's body and/or body part. In various embodiments, the method further comprises operating the system and/or various modules thereof to detect biomarkers in the subject's body and/or body part.

Various embodiments of present invention provide a computer. The computer comprises: a memory configured for storing one or more programs; and one and more processors configured for executing the one or more programs, wherein the one or more programs comprise instructions for operating a temperature management module to change and/or maintain the temperature of a subject's body and/or body part. In various embodiments, the one or more programs further comprise instructions for operating a detection module to detect biomarkers in the subject's body and/or body part.

Various embodiments of present invention provide a computer implemented method of treating, preventing, reducing the likelihood of having, reducing the severity of and/or slowing the progression of a condition in a subject. The method comprises: providing a computer as disclosed herein; connecting the computer to a temperature management module configured for changing and/or maintaining the temperature of the subject's body and/or body part; and operating the computer to operate the temperature management module to change and/or maintain the temperature of the subject's body and/or body part, thereby treating, preventing, reducing the likelihood of having, reducing the severity of and/or slowing the progression of the condition in the subject. In various embodiments, the method further comprises connecting the computer to a detection module configured for detecting biomarkers in the subject's body and/or body part, and operating the computer to operate the detection module to detect biomarkers in the subject's body and/or body part. In accordance with the present invention, "connecting" as used herein can be through wire or wireless connections, or their combinations.

Various embodiments of present invention provide a non-transitory computer-readable storage medium. The non-transitory computer-readable storage medium is configured for storing one or more programs, the one or more programs are configured for execution by one or more processors of a computer, and the one or more programs comprise instructions for operating a system and/or modules thereof to change and/or maintain the temperature of a subject's body and/or body part.

In various embodiments, the one or more programs comprise instructions for operating the system and/or modules thereof to control the temperature of the subject's body and/or body part. In various embodiments, the one or more programs further comprise instructions for operating the system and/or modules thereof to detect biomarkers in the subject's body and/or body part.

In various embodiments, the system comprises the computer. In various embodiments, the system comprises a temperature management module configured for changing and/or maintaining the temperature of the subject's body and/or body part. In various embodiments, the temperature management module comprises one or more temperature sensors configured for measuring the temperature of the subject's body and/or body part. In various embodiments, the temperature management module comprises a cooling catheter, cooling blanket, ice pack, iced lavage, transnasal cooling cannula, cooling helmet, cooling cap, cooling wrap, gel pad, or extracorporeal blood cooling machine, or a combination thereof. In various embodiments the system comprises a detection module configured for detecting biomarkers in the subject's body and/or body part.

Computers and computing devices typically include a variety of media, which can include computer-readable storage media and/or communications media, in which these two terms are used herein differently from one another as follows.

Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be appreciated that the methodologies disclosed in this specification are capable of being stored on an article of manufacture to facilitate transporting and transferring such methodologies to computer sand computing devices. The term article of manufacture, as used herein, is intended to encompass a computer program accessible from any computer-readable device or storage media.

Using various systems, computers, non-transitory computer-readable storage media as disclosed herein, therapeutic hypothermia is administered to a subject for treating, preventing, reducing the likelihood of having, reducing the severity of and/or slowing the progression of a condition in the subject. In various embodiments, the subject is a human, an infant, a child, a teenager, or an adult. In various embodiments, the condition is hypoxemia, hypoxia, ischemia, myocardial ischemia, cerebral ischemia, cardiac arrest, stroke, ischemic stroke, hemorrhagic stroke, transient ischemic attack, traumatic brain injury, traumatic spinal cord injury, hypoxic-ischemic injury, or hypoxic-ischemic encephalopathy, perinatal asphyxia, or a combination thereof. In various embodiments, the subject's body part affected by the condition is heart, brain, or spinal cord, or a combination thereof.

Many variations and alternative elements have been disclosed in embodiments of the present invention. Still further variations and alternate elements will be apparent to one of skill in the art. Among these variations, without limitation, are the selection of constituent modules for the inventive methods, compositions, kits, and systems, and the various conditions, diseases, and disorders that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

Embodiments of the invention are further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Therapeutic hypothermia (TH) is the most potent neuroprotective therapy ever studied in experimental cerebral ischemia, with multiple effects at several stages of the ischemic cascade [1]. Studies documented powerful protection with TH after accidental neonatal hypoxic-ischemic injury [2, 3] and global cerebral ischemia after cardiac arrest [4, 5]. National and international guidelines recommend TH for selected survivors of cardiac arrest, with profound benefits seen anecdotally [6]. Recently, a study comparing target temperature 33° C. to 36° C. failed to demonstrate significant effects in cardiac arrest patients [7]. This trial differed from earlier trials in that the target was not reached until much later and there was significant overlap in mean temperatures between the 2 groups. Additionally, several clinical trials of TH for head trauma and stroke have so far failed to confirm benefit in humans despite a vast pre-clinical literature [8, 9]. Therefore, it is now critical to understand the fundamental explanation for the success of TH in some, but not all, clinical trials. Based on robust pilot data, without wishing to be bound by any particular theory, we provide an explanation for the clinical trial failures of TH in human studies. This data provides critical insight that can immediately and clearly inform ongoing clinical trials of TH for both cardiac arrest and stroke [10].

The inventors performed a meta-analyses summarizing a huge preclinical literature showing that early hypothermia initiation is associated with improved outcomes in a vast number of animal studies. The most frequently used stroke models were temporary middle cerebral artery occlusion (tMCAo) (ranging between 7 and 180 minutes) or permanent middle cerebral artery occlusion (pMCAo). Target cooling temperatures ranged from 30 to 34.6° C. The duration of cooling ranged from 0 to 24 hours, and the delay to treatment start ranged from 0 to 180 minutes. Despite similar efficacy, duration of focal intra-arterial cooling was significantly shorter (mean±SE 0.61±0.23 hours, n=9) compared to whole body cooling (6.64±1.4 hours, n=61, p<0.001 by t-test). The results of the meta-analysis, shown in FIG. 1, confirm the robust pre-clinical support for TH, more than adequately satisfying STAIR, RIGOR, and CAMARADES guidelines [13-15].

It is known that the duration of TH should be adjusted based on the delay time from injury to therapy initiation, but this is never done in clinical practice [16-18]. Our own data shows that all brain cell types exhibit the same delay-duration relationship: the longer the delay to treatment, the longer duration cooling is needed to show benefit. We showed that cooling to a target-depth of 33° C. was superior to 35° C. (FIG. 2).

In addition to failure to titrate TH duration according to delay time between injury and therapy, we further believe that standard cooling/warming schedules failed in human clinical trials due to unappreciated aspects of cerebral pathophysiology, notably the interaction between neurons and astrocytes and maintenance of homeostasis (energy metabolism, neurotransmitter release and signal transmission) during physiological and pathological events in the brain. Considerable data has emerged to show that different elements of the neurovascular unit (NVU) behave quite differently during injury: astroctyes tolerate substrate deprivation (removal of oxygen and glucose) longer than neurons, with endothelial cells intermediate. We recently discovered that astrocytes subjected to substrate deprivation (preconditioning) produce a transferable, heat-labile, trypsin-digestible factor that protects neurons from similar substrate deprivation. Other protective effects of astrocytes have been documented as well [19-28], but the mechanism is not yet fully established and we are the first to show the protective effect of preconditioned astrocytes is transferable (paracrine). Astrocyte mediated protection of neurons can be blocked by incubating the astrocytes at 33° C. for prolonged periods, whereas incubation at 35° C. doesn't alter the protective astrocyte paracrine effect as much (FIG. 3). Thus, in the human stroke or head trauma patient, single-target hypothermia for a fixed duration, followed by a fixed ramp re-warm, could inhibit neuroprotective activity in the NVU.

The net effect, despite robust hypothermic protection of neurons, could be unfavorable due to inhibited NVU mediated protective responses.

Therefore, for two reasons, namely the need to titrate duration/depth based on delay, and the differential effects of TH on different cell types, the inventors provide treatment methods in which TH is carefully optimized. In contrast to the methods described herein, in all clinical trials TH has been administered at one target temperature (e.g. 33° C.) for a fixed duration (e.g. 24 hours), followed by a gradual "ramp" re-warm to normothermia. In several clinical trials published to date (stroke, head trauma), TH has failed to show benefits commensurate with the benefit predicted from animal studies, perhaps due to failure to optimize the administration of TH so as to preserve the protective NVU effect on neurons.

Figure 4:
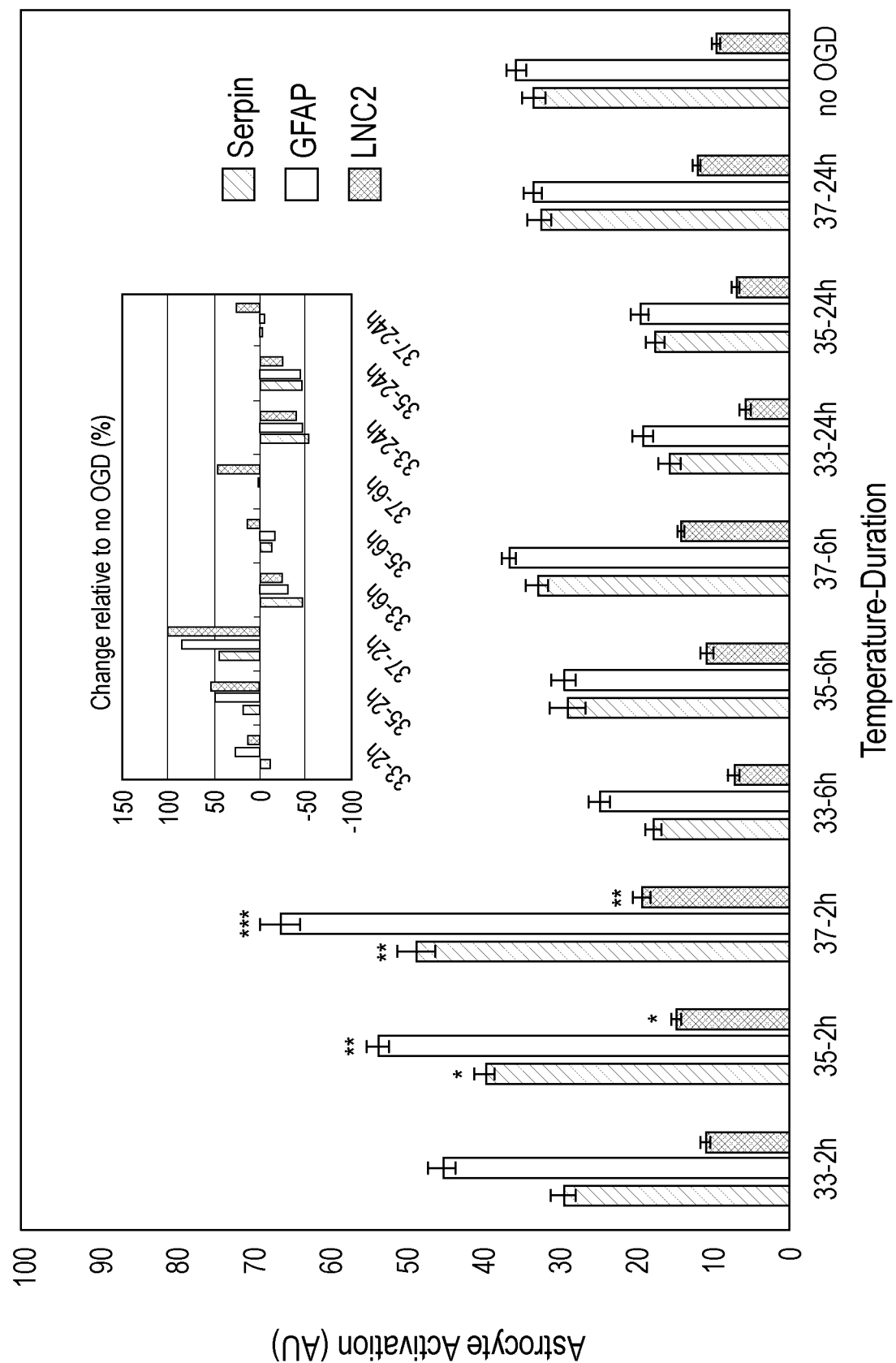
FIG. 4 depicts in accordance with various embodiments of the invention, protective effect of hypothermia mediated by astrocytes is directly linked to the activation of astrocytes tagged by activation markers such as GFAP, SERPIN-A3N and LNC2. Astrocytes cultures were subjected to OGD for various time points 2, 6 and 24 hours at 33, 35 and 37° C. Post-OGD cells were fixed using 4% paraformaldehyde and immunoassayed for astrocyte activation markers. The activation of astrocytes was assessed by measuring the fluorescence of individual proteins using NIH Fiji software and the fluorescence and laser intensities were kept constant for all the conditions. Astrocytes subjected to 3 hour OGD at 35 and 37° C. showed significant activation in all three proteins intensity when compared to no-OGD control samples (ANOVA, Dunnett's *$p<0.001$, $p<0.01$ and *$p<0.5$). Inset-relative change in fluorescence intensity compared to no-OGD control cells.

Astrocytes confer protective effects during hypothermia. As shown in FIG. 4, protective effect of hypothermia mediated by astrocytes is directly linked to the activation of astrocytes tagged by activation markers such as GFAP, SERPIN-A3N and LNC2. Astrocyte activation, as documented by these three measures, is associated with astrocyte protection of neurons.

Figure 5:
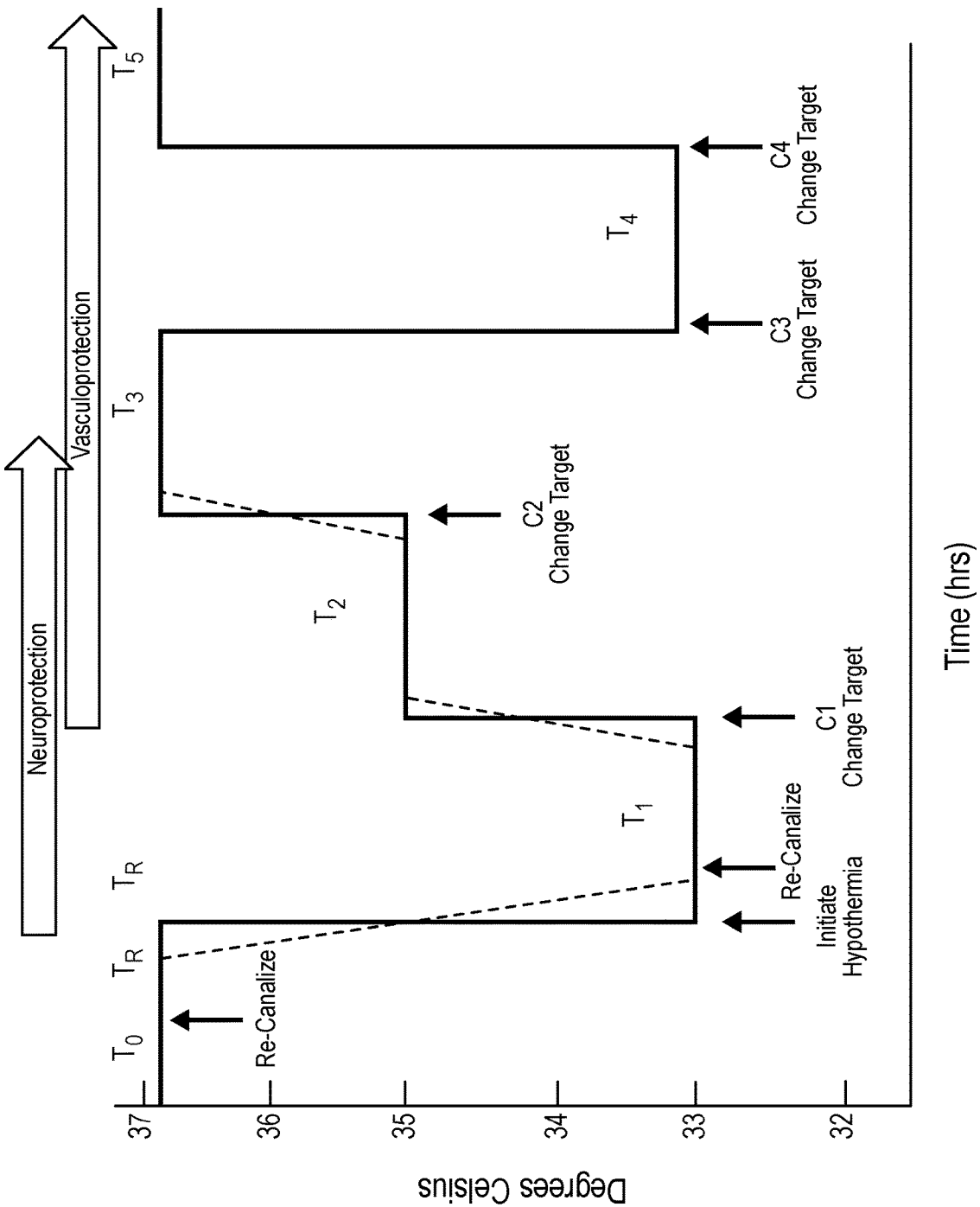
FIG. 5 depicts, in accordance with various embodiments of the invention, staircase method for optimized therapeutic hypothermia. The critical time epochs in TH are as follows: T0=Occlusion time, i.e. time from onset of ischemia (or other injury) to the time of reperfusion; TR=Reperfusion time, i.e. time from recanalization or ROSC to initiation of TH; T1=time at deepest target, for example time at 33° C.; T2=time at next target, for example time at 35° C.; and T3=time at controlled normothermia. The critical transitions during TH are as follows: C0: initiate hypothermia is the time at which cooling begins; C1: change to higher target temperature; C2: change to normothermia; and further changes include re-cooling for edema management (C3) and final return to normothermia (C4). The dashed lines represent the actual transitions that may require time to move from one core body temperature to the next. TH immediately after reperfusion represents neuroprotection, while later cooling may target edema management and vasculoprotection. In some embodiments, hypothermia TH could be initiated before recanalization, which would result in reaching to target temperature at T1 before TR.

We provide an alternative, highly novel approach to TH that we have named "the staircase method for optimized therapeutic hypothermia" (FIG. 5). The principles of the staircase method include: (1) To optimally protect ischemic brain, the duration of hypothermia is a function of the delay time to restoration of blood flow; (2) The duration of hypothermia is also a function of the delay to TH initiation; (3) Time spent at the deepest target temperature is limited to the briefest possible; (4) Rather than ramp rewarming, target temperature is increased in discrete steps at intervals that can be personalized to individual patients based on either formulae or biomarkers, as described herein.

The total duration of hypothermia includes the time spent at the deepest target temperature as well as any time spent re-warming. The total time is calculated based on knowledge of the duration of ischemia and delay time to TH onset. Time spent at the deepest temperature is limited to avoid collateral complications of TH (pneumonia, other infections) but also to avoid inhibiting protective effects from the NVU. Using step increases, rather than ramp warming, allows precise control of the time spent at each temperature to achieve optimal protection. In addition to these principles, biomarkers (for example, cold shock proteins) are used to signal the appropriate transitions to the next temperature.

We created novel in vitro and in vivo models to study effect of hypothermia on elements of the NVU (such as neurons, astrocytes, endothelial cells and pericytes) as well as transgenic animals to allow more focused investigation [29]. For example, we have shown differential effects of various neuroprotectants on endothelial cells, astrocytes and neurons [30, 31]. We cultured all 3 cell types in monocultures and confirmed that (i) hypothermia powerfully protected all 3 cell types; (ii) 33° C. was superior to 35° C. regardless of duration; and (iii) the same depth-delay-duration relationship was seen in astrocytes and endothelial cells as shown for cultured neurons in FIG. 2. To simulate the interplay between the different components of NVU, co-cultures or transwell insert cultures are harnessed to understand the cell-cell interface. Our novel in vitro approach allows rapid replication; multiple depth/duration/delay study groups; and ultimately extensive mechanistic studies.

Primary neuronal cells were isolated from E16-E17 embryos and primary astrocytes and endothelial cells were isolated form P0-P1 pups. The cells were grown for 8-10 days for further experiments. After 2 h of OGD in primary neuronal cultures we measured the protective effect of hypothermia (33° C. or 35° C.) for various durations (2 h, 6 h, or 24 h) using 3-(4,5-dimethylthiazol-2-yl)-2,5-diphenyltetrazolium bromide (MTT) and lactate dehydrogenase (LDH) assay[21, 32]. As shown in FIG. 2, immediate hypothermia (no delay) conferred neuroprotection at all durations and target-depth 33° C. was superior to 35° C. hypothermia regardless of treatment duration. When hypothermia was initiated 90 min after 2 h OGD we found that 6 and 24 h but not 2 h treatment duration showed significant protection. Regardless of depth and duration, both levels of hypothermia were superior to normothermia in neurons, astrocytes and endothelial cells.

Figure 6A:
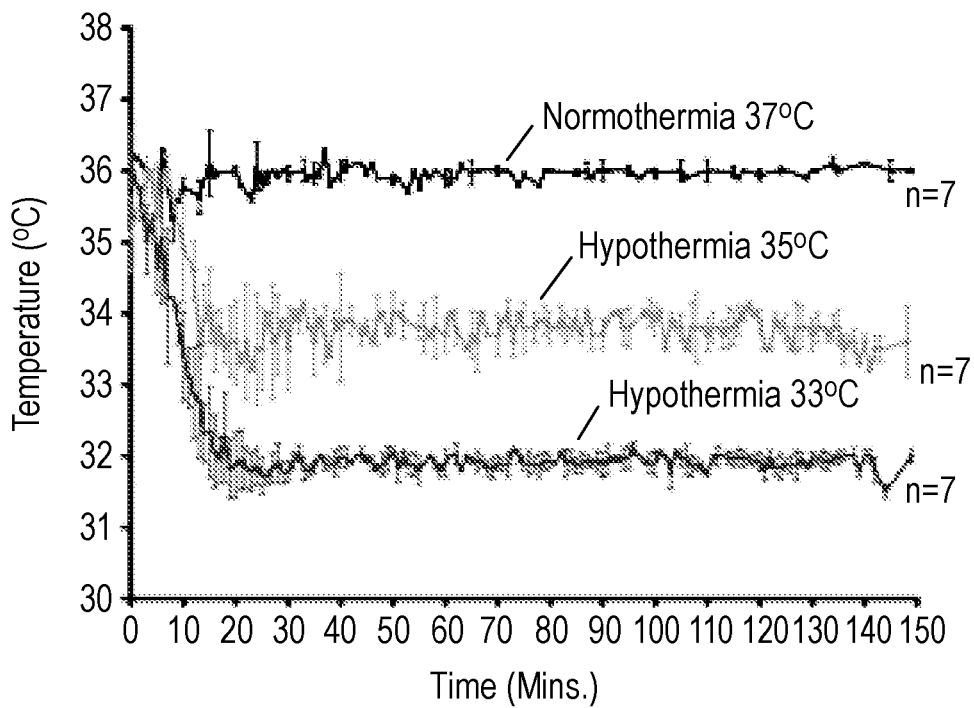
FIG. 6A-FIG. 6C depict, in accordance with various embodiments of the invention, schematic showing the proposed perivascular hypothermia model. The perivascular catheter filled with cold saline is inserted into the abdomen and placed around inferior vena. Catheter saline circulated into the ice water bath; body temperature is controlled by varying the flow rate using the peristaltic pump. The animal temperature is monitored with a thermistor implanted in the temporalis muscle (FIG. 6C). The graph (FIG. 6A) shows temperature (mean±SE) 150 min. Temperature rapidly dropped to 33° C. or 35° C. in 12 min and was stably maintained within a tight range. Ultrafast transitions, step changes were easily accomplished within 5-10 min.
Figure 6B:
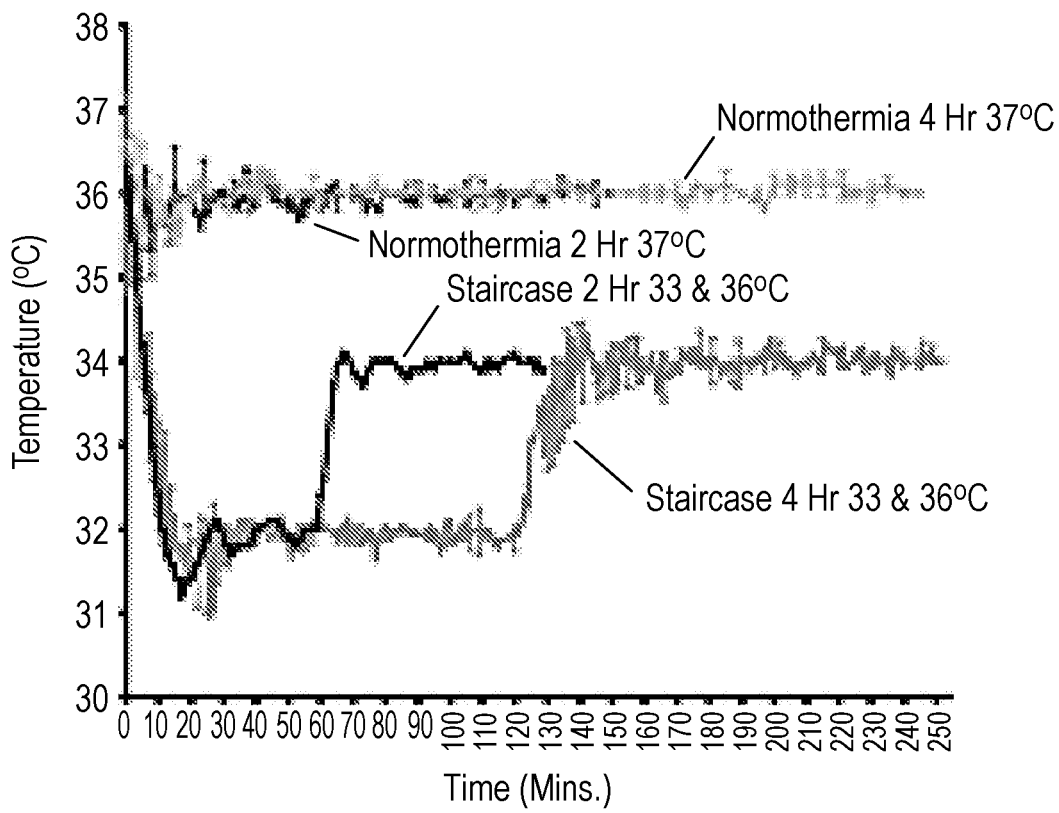
Figure 6C:
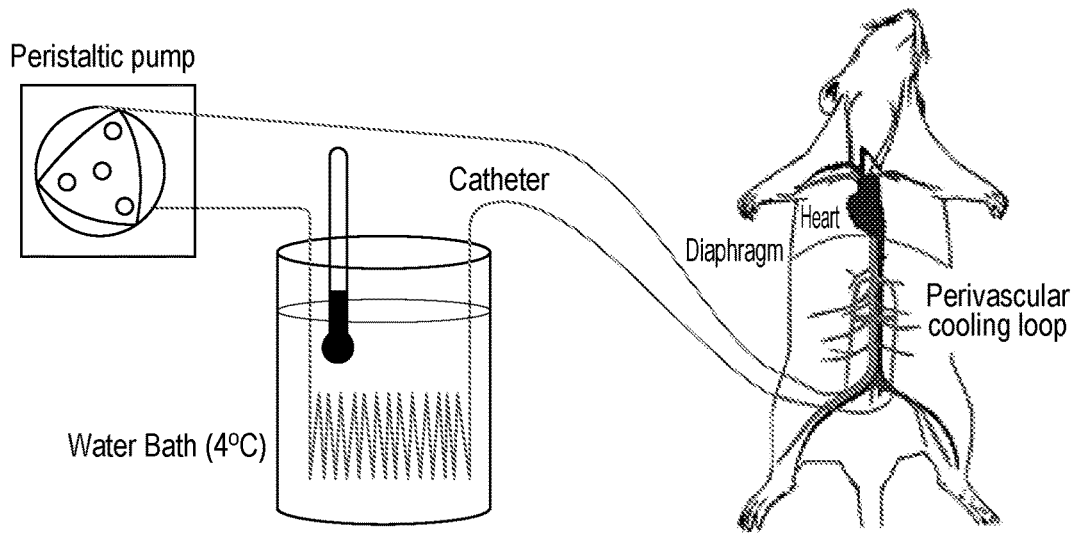
Figure 7:
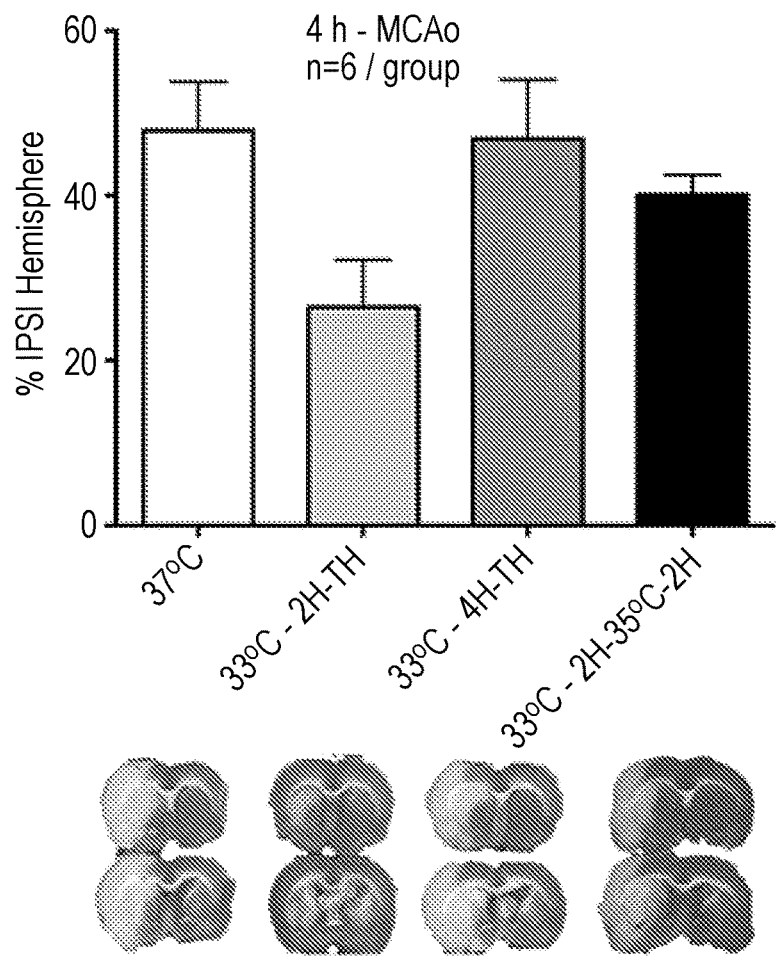
FIG. 7 depicts, in accordance with various embodiments of the invention, the effect of hypothermia depth/duration on infarction. Animals were subjected to 4 hours of MCAO and randomly assigned to either 2 or 4 hours of hypothermia at 33° C. immediately after reperfusion. Animals treated for 2 hours had significantly smaller infarction, *$p<0.05$, compared to control and 4 hours of hypothermia animals. The 4 hours staircase was not statistically significantly better.

We have shown close correlation between cortical brain temperature and temporalis or core body temperature, by comparing telemetered brain temperature (Mini-Mitter XM-FH) to core body temperature [36]. Using a bioassay method we developed [36-38], we demonstrated considerable neuroprotection from cooling to 34° C. temporalis (33° C. brain) for as short as 2 h. We recently developed a novel perivascular method for cooling rodents that allows ultrafast transitions and tight temperature controls (FIG. 6). In this new model, the transition from 37.5° C. to 33° C. requires about 10 min. Our data shows significant decrease of ischemia and infarct reduction in rats subjected to 4 hour middle cerebral artery occlusion (MCAO) followed by immediate cooling at 33° C. for 2 hours, $p<0.05$ * with TTC staining when compared to normothermia animals. However no difference was observed when the normothermia animals were compared to another group of animals cooled for 4 hour at 33° C. after 4 hour MCAO (FIG. 7). The results from our in vitro and in vivo experiments support the validity of the staircase approach. We further determine whether the staircase approach to TH proves superior to a traditional approach and initiate characterization of needed biomarkers.

The total duration of hypothermia includes the time spent at the deepest target temperature, as well as any time spent re-warming. The total time could be calculated based on knowledge of the duration of injury. Time spent at the deepest temperature should be limited to avoid collateral complications of therapeutic hypothermia (pneumonia, other infections) but also to avoid inhibiting protective effects from astrocytes. Using step increases, rather than ramp warming, should allow precise timing of the time spent at each temperature needed to achieve optimal cooling. In addition to these principles, biomarkers can also be found to signal the appropriate transitions to the next temperature. The staircase method is defined in FIG. 5.

The critical time epochs in therapeutic hypothermia are as follows: T0=Occlusion time—time from onset of ischemia (or other injury) to the time of reperfusion; TR=Reperfusion time—time from recanalization to initiation of therapeutic hypothermia; T1=time at deepest target—for example 33° C.; T2=time at next target—for example 35° C.; T3=time at controlled normothermia; T4=time at deep hypothermia for edema control; T5=time at controlled normothermia after edema.

The critical transitions during therapeutic hypothermia are as follows: Onset of ischemia (stroke, cardiac arrest, head trauma) is set as Time=0; Reperfusion (recanalization, ROSC); Initiate hypothermia is the time at which cooling begins; C1 Change to higher target temperature; C2 Change to normothermia; C3 Return to deep therapeutic hypothermia if needed for edema control; C4 Final return to normothermia.

There are two approaches to identifying the critical times to make transitions from one target temperature to the next, that is to say, estimating the time needed at 33° C. (we call T1) and the time needed at 35° C. (we call T2). First, there may be a quantitative relationship between ischemia duration (T0) and the total time needed for therapeutic hypothermia (T1+T2). For example, the total duration of therapeutic hypothermia could be a multiple of the occlusion time:

$$(T1+T2)=xT0$$

In this equation, the total time spent in TH would equal a multiple, x, of the occlusion time, T0. In some situations, however, therapeutic hypothermia cannot begin immediately after restoration of blood flow, e.g., after return of spontaneous circulation (ROSC). For example, total duration of TH can be a multiple of occlusion time T0 plus a multiple of the time before initiation of therapy, TR, such that:

$$(T1+T2)=xT0+yTR.$$

Our first approach tests ranges of T1 and T2 for given inputs of T0 and TR, and derives values for x and y that yield the best survival in 2 different types of cell cultures: coculture and transwell. Rather than check all permutations, we provide a numeric sequence that could prove optimal during empiric testing. For example, a simple sequence 1-2-3 may prove valuable such that x=2 and y=3. Other candidate sequences include an exponential (1-4-9) sequence, or a Fibonacci sequence (1-2-3-5-8). How to relate T1, the time at 33° C., vs T2, the time at 35° C., can be simplified as well, by the following equation:

$$fT1+(1-f)T2=\text{total cooling time}$$

Here, f varies from 0 to 1 in graded fractions and find the value that yields the best survival.

The second approach involves biomarkers that indicate the optimum time for the key transitions C1 and C2 (FIG. 5). There are measurable proteins, chemokines, and metabolites that could signal when to raise or lower the target temperature. For example, several lines of evidence suggest that during hypothermia, mammalian cells express cold shock proteins that provide considerable resistance to further injury. To date, the most widely studied cold shock proteins are the RNA Binding Motif Protein 3 (RBMP3), and the Cold Injury RNA Binding Protein (CIRB)[39-42]. In bacterial, fungal, and protozoal cells, however, a much larger array of cold shock proteins exist, few of which have been studied in mammalian cells[43]. Without wishing to be bound by any particular theory, we believe that once neurons begin a robust synthesis of cold shock protective proteins, the target temperature could be changed to a warmer temperature, C1, so as to allow astrocytes (and perhaps other elements of the NVU) to begin manufacturing paracrine protective factors. Similarly, once the NVU is producing sufficient quantities of a paracrine protective factor, the transition to controlled normothermia, C2, could begin safely. These markers could solve the key dilemma facing clinical TH: that it works powerfully in small laboratory species, but not in human patients and there is no known method for titrating TH in patients.

In actual practice, the transition from one target temperature to the next cannot be instantaneous, as illustrated by the dashed lines in FIG. 5. In recent clinical trials and in current clinical practice, the time to reach target temperature ranges over several hours. During the ramp rewarm phase currently used (essentially a prolonged C1+C2), the lengthy transition is intentional. In our methods, early and deep therapeutic hypothermia followed by an interval at milder temperatures allows the NVU time to generate protective factor, and it is critical to make the transitions as brief as possible, for example, ultra-brief transitions from normothermia to deep hypothermia, followed by precise control at intermediate steps.

We developed a peri-vascular method for cooling rodents during middle cerebral artery occlusion that similarly allows ultrafast transitions. In this new model, the transition from 37.5° C. to 33° C. requires about 15 min. The method could be applied easily to rodent models of cardiac arrest, myocardial ischemia, or head trauma. This model facilitates the characterization of the staircase method and the discovery of needed biomarkers.

Figure 9:
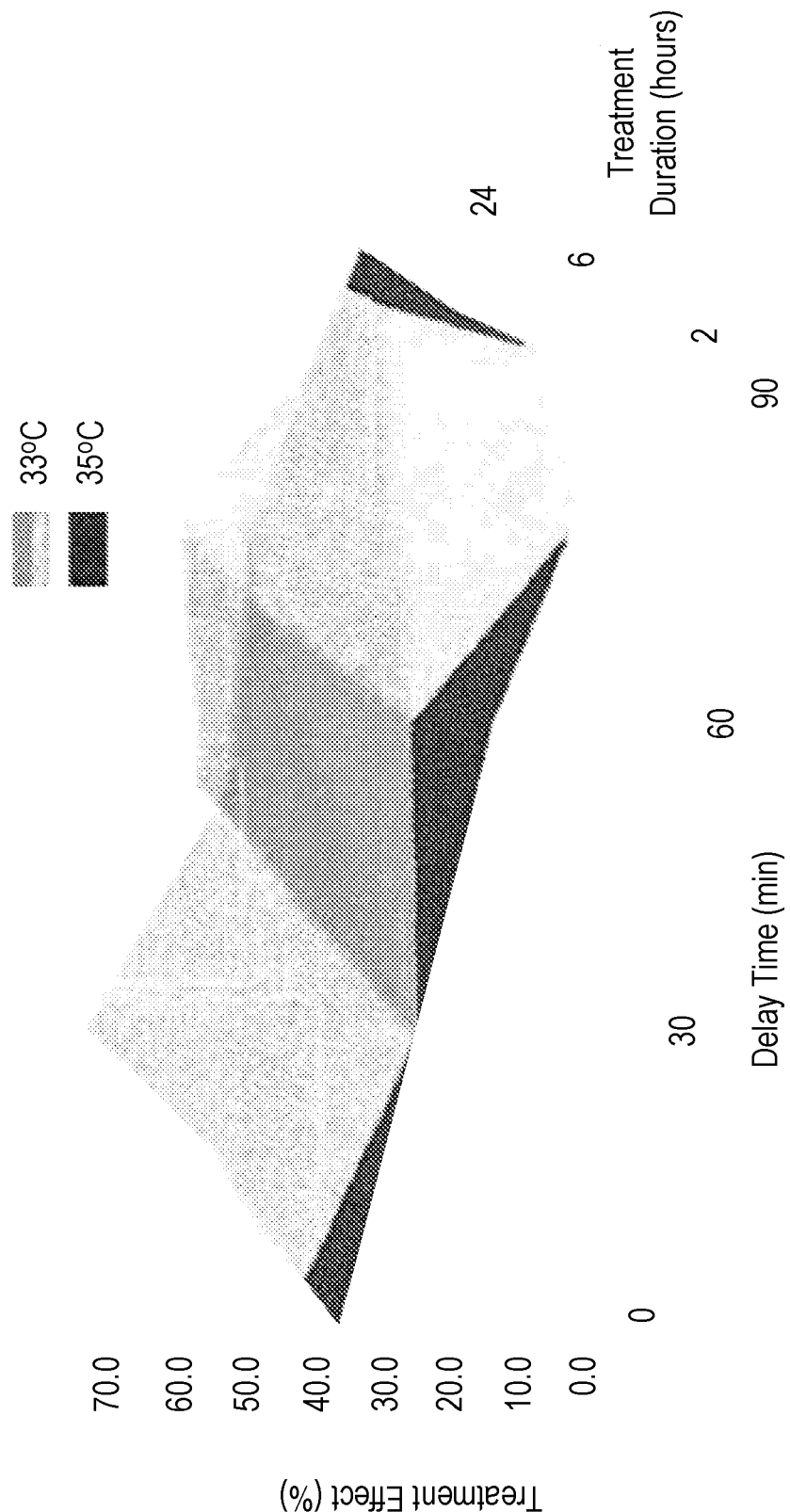
FIG. 9 depicts, in accordance with various embodiments of the invention, a relationship among target depth, delay, and duration for neurons challenged with 2 hours substrate deprivation (T0=2).

The approach to deriving the linear multiples of occlusion time (finding x and y) can be simplified. In pilot studies, in which we fixed T0 at 2 hours of neuronal OGD, we varied TR from 0 to 90 min (FIG. 9). We confirmed that in fact the longer TR (Delay Time: x-axis), the longer the total duration of therapeutic hypothermia needed (Treatment Duration: y-axis). In these experiments, the target temperature was fixed at either 33° C., 35° C., or 37° C. The Treatment Effect size (z-axis) is the difference between either of the two targets, and 37° C. The target-depth, delay, duration relationship for neurons challenged with 2 hours substrate deprivation (T0=2) is illustrated in FIG. 9. Shorter delays (shorter TR), or longer treatment times (T1) yield superior treatment effects.

To estimate the needed x and y in monocellular cultures, we vary T0 from 0 to 120 minutes and TR from 0 to 90 min because these are very clinically relevant times for ischemia and reperfusion duration prior to therapeutic hypothermia beginning. We vary x and y (0, 1, 2, or 3) and study the survival of cells using cell viability and cell death assays. Further, we simplify the derivation by testing a fixed relationship between T1 and T2:

$$fT1+(1-f)T2=xT0+yTR$$

In this equation, we make the assumption that T1 and T2 are related in order to simplify the design of all subsequent experiments. We vary f over a range (0, ⅓, ½, ⅔, 1) to explore the effect of a staircase step of varying intervals. As an example, a prototypical experiment is designed as follows:

$$f=½, x=1, y=2$$

| T0 | TR | T1 + T2 | T1 | T2 |
|---|---|---|---|---|
| 0 | 0 | 0 | 0 | 0 |
| 30 | 0 | 30 | 9.9 | 20.1 |
| 60 | 0 | 60 | 19.8 | 40.2 |
| 90 | 0 | 90 | 29.7 | 60.3 |
| 120 | 0 | 120 | 39.6 | 80.4 |
| 0 | 30 | 60 | 19.8 | 40.2 |
| 30 | 30 | 90 | 29.7 | 60.3 |
| 60 | 30 | 120 | 39.6 | 80.4 |
| 90 | 30 | 150 | 49.5 | 100.5 |
| 120 | 30 | 180 | 59.4 | 120.6 |
| 0 | 60 | 120 | 39.6 | 80.4 |
| 30 | 60 | 150 | 49.5 | 100.5 |
| 60 | 60 | 180 | 59.4 | 120.6 |
| 90 | 60 | 210 | 69.3 | 140.7 |
| 120 | 60 | 240 | 79.2 | 160.8 |
| 0 | 90 | 180 | 59.4 | 120.6 |

-continued

| T0  | TR | T1 + T2 | T1   | 12    |
|-----|----|---------|------|-------|
| 30  | 90 | 210     | 69.3 | 140.7 |
| 60  | 90 | 240     | 79.2 | 160.8 |
| 90  | 90 | 270     | 89.1 | 180.9 |
| 120 | 90 | 300     | 99   | 201   |

The rows marked T0-0 are in fact the controls: there is no injury (no substrate deprivation) applied. All experiments are conducted in 6 well plates, and the final results averaged for the plate. Generally the experiments covering one OGD duration (one value for T0) can be completed in 1 day, and there are 5 durations (5 different values for T0) per table; one table takes about 1 week to complete. Additional tables can be generated using different values for x, y, and f for which there are 80 possible combination (x=0, 1, 2, 3; y=0, 1, 2, 3; f=0, ⅓, ½, ⅔, 1), so the entire exercise requires 80 weeks.

From these results we are be able to derive the optimal x, y, and f. On the other hand, it may emerge that the best results obtain when T1 or T2 is fixed at one values, e.g. 2 hours. In this case, we would explore some of the numeric sequences mentioned above. In either event, by exploring a wide range of values for x, y and f a clear picture should emerge to guide the design of an optimum staircase.

Next, we confirm the optimum values for f x and y in co-cultures. Astrocytes and neurons are grown together, then subjected to deprivation of oxygen and glucose for variable durations (T0) exactly as above. The protective effect of astrocytes then is immediately available in the culture media to the neurons since they share the same culture medium. As above, we use cell viability assays on the neurons, to confirm the optimal values for f x and y. The values for x and y derived from monocellular cultures and from co-cultures should be reasonably close. Otherwise, there is an interaction effect among cells in the NVU.

Finally, using a rodent MCA occlusion (MCAO) model, we test an optimized staircase method using the f x and y derived from the co-culture experiments. In this model, the main outcome is stroke size, estimated with histological staining, and behavioral performance of the animals in various cognitive and motor tasks. It is not practical to repeat full exploration of the optimum values for x and y the in vivo MCAO experiments, so only a few values are selected to confirm the optimum schedule.

From this work, it emerges that there is a relationship among the duration of therapeutic hypothermia needed to salvage neurons after a given delay, using 2 (or more) levels of target temperature (FIG. 5). The optimum design of the staircase may involve fixed values for f, x and y, and/or the derivation of biomarkers Agnostic Proteomic Assessment of Neuroprotection During TH The proteome from blood, cerebrospinal fluid (CSF) and brain tissue has been used to identify biomarkers as well as to understand the pathogenesis of ischemic disease[44-47]. We use an agnostic proteomic approach to assess the global effects of hypothermia on various cell types from mono, mixed or transwell culture. Since various cells from NVU have a wide range of proteomic profile we use all the cell types from different cultured conditions exposed to OGD followed by different degrees of hypothermia.

Figure 8:
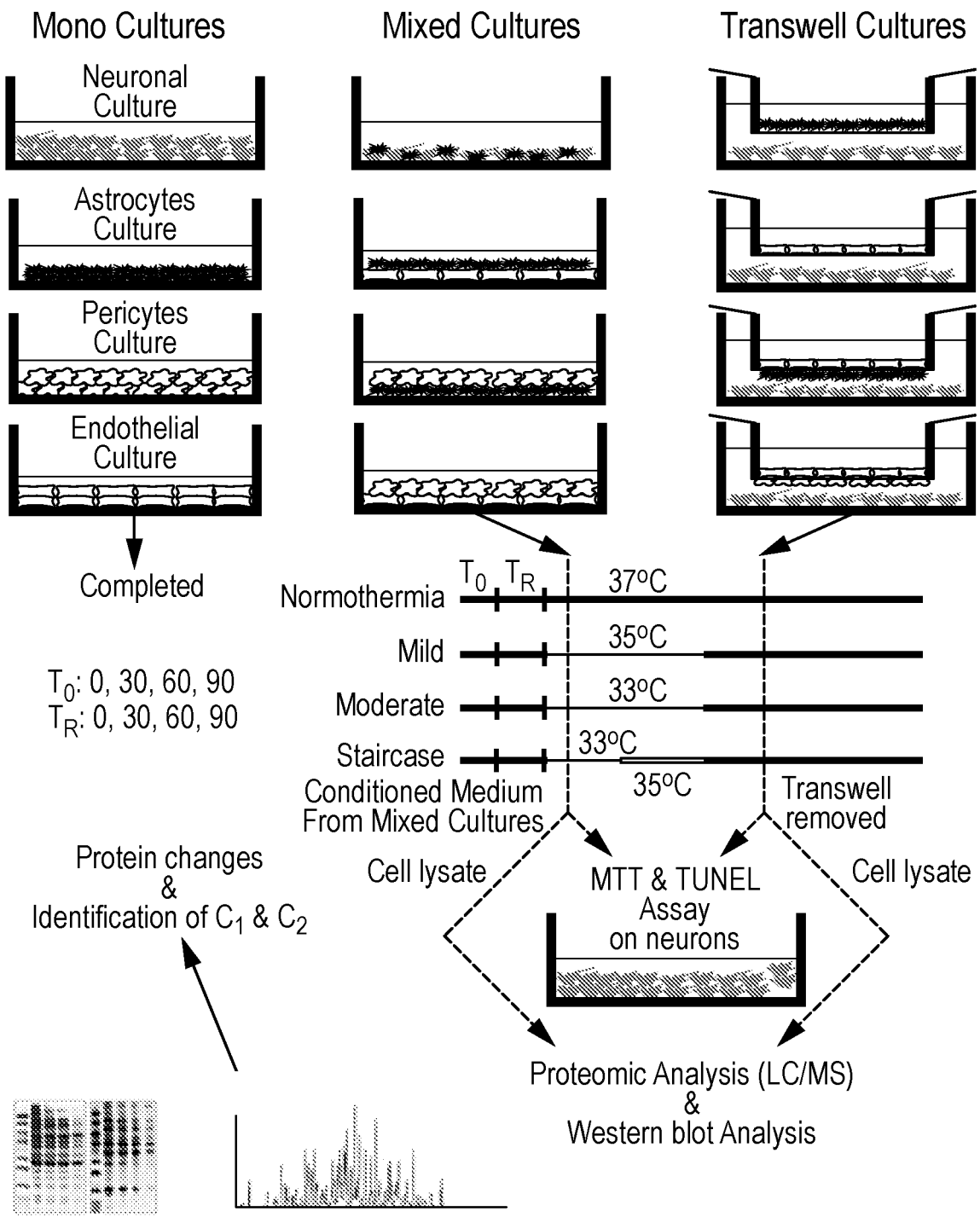
FIG. 8 depicts, in accordance with various embodiments of the invention, design overview to study the effect of therapeutic hypothermia post ischemia in mono, mixed and transwell culture system. The cells systems are subjected for various time points of OGD and varying degree of hypothermia. Conditioned medium is used to elucidate the effect of NVU on neuronal survival, whereas the cell lysate is used to determine the changes in proteomic profile, changes in protein expression. Conditioned media are subjected to LC/MS to identify the $C_1$ and $C_2$ biomarkers.

As described in the schematic FIG. 8, cell lysate is obtained from various mixed and transwell cultures and protein concentration is determined by bicinchoninic acid (BCA) assay. An in-solution digest of the protein is performed using trypsin after reduction and alkylation of cysteine disulfide bonds. The digested sample is acidified with formic acid, desalted, and dried using a Speedvac. Dried samples are reconstituted in buffer A (0.1% formic acid in H2O) and analyzed by LC-MS/MS on an Orbitrap Elite (Thermo Scientific). Samples are loaded onto a C18 column maintained at 40° C. for the chromatographic separation of peptides. Peptides are eluted based on hydrophobicity using 0-80% increase in solvent B, 0.1% formic acid in acetonitrile over solvent A, water with 0.1% formic acid over 120 min at 300 nL/min. A top 10 data-dependent acquisition method is used and the files are searched using multiple search algorithms including Comet and X! Tandem through the Trans-Proteomic Pipeline. Using false discovery rate and high-quality score cutoff, only high-confidence data is used for downstream analysis. After protein identification and label-free quantification, UniProt accession numbers and fold changes of the differentially expressed proteins are imported into ingenuity pathways analysis (IPA, Ingenuity Systems) for proteome network analysis alongside other in-house methods. Statistical significance of each network or list is determined by IPA using a Fisher exact test ($p<0.05$) and is used for pathway creation that can be used to model our MS-based proteomic data.

From the proteomic analysis on different cell type we can identify up-regulated and down-regulated proteins during ischemic injury and effect of hypothermia and its involvement in neuroprotection, metabolic storage, morphological changes, cell migration, and responses to inflammation. From the above experiments we can identify changes in cold-shock proteins like RBMP3 and CIRB3, inflammatory and cytoskeletal markers which further help us in identifying the biomarkers (C1 and C2) to switch the depth and time point of hypothermia (T1 and T2).

Confirmation of Cold-Shock Protein Biomarkers

We use Western blot analysis to determine whether, in fact, hypothesized cold-shock proteins do associate with successful TH conditions. The total protein concentration of the membrane protein extract for receptors and tissue lysate for signaling pathways is determined by Bradford protein assay. 15 µg of total protein is fractionated by electrophoresis on 10% SDS-PAGE, and transferred onto 0.2 µm-nitrocellulose membrane. The membrane is blocked with 5% non-fat dried milk at room temperature for 1 h and incubated overnight at 4° C. with specific primary antibodies against inflammatory markers, cold shock proteins (RBMP3 and CIRB3), phospho and total PI3K, CREB, ERK1/2 and PKC-α. Following three subsequent washes, the membrane is incubated with peroxidase conjugated goat anti-rabbit or goat antimouse secondary antibody at room temperature for 1 h. The bands are detected using chemiluminescence reagent and images are taken using a BIO-Rad ChemiDoc™ XRS imaging system. β-actin is used as the housekeeping protein for loading control. The band's intensity is quantified using densitometric analysis and the changes in protein expression calculated as the ratio of the band of interest relative to the density of β-actin.

Effect of Target-Depth, Duration, and Delay on Behavioral Outcome Using MCAO

Using our rodent MCA occlusion model[48], we test an optimized staircase method using the best f, x and y derived from the co-culture and trans-well experiments. A few values are selected to confirm the optimum schedule. In the MCAO model, the de-occlusion of the nylon filament replicates the recanalization now seen routinely after neurothrombectomy with or without intravenous rt-PA[49-52]. The main outcome is stroke size, estimated with histological staining, and behavioral performance of the animals in various cognitive and motor tasks. From this work, there is a relationship among the duration of TH needed to salvage neurons after a given delay, using 2 (or more) levels of target temperature (FIG. 5). We determine that the optimum design of the staircase involves fixed values for f x and y, or the derivation of biomarkers. Eventually clinical trials establish the values for f x and y, that appear best in rodents are the same or may be modified in humans. Another important result from these rodent studies is the confirmation of the delay-depth-duration relationship and the efficacy of the staircase method (FIG. 5). Blood and brain tissue lysate are collected for proteomic analysis. Any biomarkers for C1 and C2 are confirmed from this material using Western blot or ELISA.

Reversible MCAO (male and female adult Sprague-Dawley, 290 to 310 g) is induced for 2 h using a filament[48]. Using the novel in vivo perivascular hypothermia model developed in our lab (FIG. 7) rats are randomized to one of the study groups to determine the effect of duration, depth, delay or using the x, y, and f as discussed above. Alternative values are selected, at random, to determine if better results are obtained with shorter or longer times spent at the steps in the staircase. After 48 h the animal is rated (modified Bederson scale) by an examiner blind to treatment group status. The brain is removed, sectioned and stained with triphenyltetrazolium chloride (TTC); lesion size is estimated using planimetry by an examiner blind to treatment status [30, 37, 48].

Power analysis of behavioral curves, assuming alpha=0.05 and beta=0.90, a coefficient of variation (CV) of 15% and a difference between means of 20%, we need a sample size of 14 animals per group. We include 20 animals per group due to premature loss caused by preparation difficulties or death following stroke (before a treatment can be administered)[36-38, 53]. Animals that do not survive through treatment are excluded from the final analysis. For quantitative lesion volume studies using TTC staining, assuming a CV of 75%, alpha=0.05 and beta=0.90, a difference between means of 50%, we need 40 animals per group. The markedly improved heterogeneity of infarct size following MCAO in our lab yields a substantially smaller CV than typical [37].

The x, y and f as discussed above may yield the optimal result in the in vivo model, using TTC and behavioral outcome measures. On the other hand, we may find either different values, or that fixed durations for T1 and T2 (as are used clinically) provide the best results. For the first time we fully characterize and confirm the relationship among TH depth, duration and delay using a clinically relevant model with behavioral and histological endpoints[14, 54]. Prior studies have suggested this complex relationship, but clinical trial designs have not incorporated a duration adjustment based on delay time. Patients who arrive early may only need short durations at 33° C. followed by 35° C. for an additional duration, while patients with longer ischemia times (longer T0) may need longer cooling times (longer T1 or T2 or both). Additional study groups can be added to those proposed, but we may include only as many groups as needed to answer the clinical question; the data provide a comprehensive survey of the depth-delay-duration relationship; and we can confirm these findings using more detailed histology and extensive histological analysis[30, 37].

REFERENCES

1. Wu T C, Grotta J C. Hypothermia for acute ischaemic stroke. Lancet Neurol. 2013 March; 12(3):275-84. PubMed PMID: 23415567.
2. Shankaran S, Laptook A R, Ehrenkranz R A, Tyson J E, McDonald S A, Donovan E F, et al. Whole-body hypothermia for neonates with hypoxic-ischemic encephalopathy. N Engl J Med. 2005 Oct. 13; 353(15):1574-84. PubMed PMID: 16221780.
3. Johnston M V, Fatemi A, Wilson M A, Northington F. Treatment advances in neonatal neuroprotection and neurointensive care. Lancet Neurol. 2011 April; 10(4):372-82. PubMed PMID: 21435600. Epub 2011/03/26. eng.
4. Bernard S G, Buist M D, Jones B M, Silvester W, Gutteridge G, Smith K. Treatment of comatose survivors of out-of-hospital cardiac arrest with induced hypothermia. New Engl J Med. 2002; 346:557. PubMed PMID: 5069.
5. The Hypothermia After Cardiac Arrest Study G. Mild therapeutic hypothermia to improve the neurologic outcome after cardiac arrest. New Engl J Med. 2002; 346: 549. PubMed PMID: 5067.
6. Nolan J P, Morley P T, Vanden Hoek T L, Hickey R W, Kloeck W G, Billi J, et al. Therapeutic hypothermia after cardiac arrest: an advisory statement by the advanced life support task force of the International Liaison Committee on Resuscitation. Circulation. 2003 Jul. 8; 108(1):118-21. PubMed PMID: 12847056.
7. Nielsen N, Wetterslev J, Cronberg T, Erlinge D, Gasche Y, Hassager C, et al. Targeted Temperature Management at 33 degrees C. versus 36 degrees C. after Cardiac Arrest. N Engl J Med. 2013 Nov. 17. PubMed PMID: 24237006.
8. Andrews P J, Sinclair H L, Rodriguez A, Harris B A, Battison C G, Rhodes J K, et al. Hypothermia for Intracranial Hypertension after Traumatic Brain Injury. N Engl J Med. 2015 Oct. 7; 10.1056/NEJMoa1507581. PubMed PMID: 26444221.
9. Clifton G L, Miller E R, Choi S, Levin H S, McCauley S, Smith K R, et al. Lack of effect of induction of hypothermia after acute brain injury. N Engl J Med. 2001; 344(8): 556. PubMed PMID: 4854.
10. Lyden P D, Hemmen T M, Grotta J, Rapp K, Raman R. Endovascular therapeutic hypothermia for acute ischemic stroke: ICTuS 2/3 protocol. Int J Stroke. 2013 Nov. 10. PubMed PMID: 24206528.
11. van der Worp H B, Macleod M R, Kollmar R. Therapeutic hypothermia for acute ischemic stroke: ready to start large randomized trials? J Cereb Blood Flow Metab. 2010 June; 30(6):1079-93. PubMed PMID: 20354545. Pubmed Central PMCID: 2949207. Epub 2010/04/01. eng.
12. van der Worp H B, Sena E S, Donnan G A, Howells D W, Macleod M R. Hypothermia in animal models of acute ischaemic stroke: a systematic review and meta-analysis. Brain. 2007 December; 130(Pt 12):3063-74. PubMed PMID: 17478443.
13. Lapchak P A, Zhang J H, Noble-Haeusslein L J. RIGOR Guidelines: Escalating STAIR and STEPS for Effective Translational Research. Transl Stroke Res. 2013 June; 4(3):279-85. PubMed PMID: 23658596. Pubmed Central PMCID: 3644408.
14. Fisher M, Feuerstein G, Howells D W, Hum P D, Kent T A, Savitz S I, et al. Update of the stroke therapy academic industry roundtable preclinical recommendations. Stroke. 2009 June; 40(6):2244-50. PubMed PMID: 19246690. Epub 2009/02/28. eng.
15. Macleod M R, Fisher M, O'Collins V, Sena E S, Dirnagl U, Bath P M, et al. Reprint: Good laboratory practice: preventing introduction of bias at the bench. Int J Stroke. 2009 February; 4(1):3-5. PubMed PMID: 19236488. Epub 2009/02/25. eng.

16. Colbourne F, Corbett D, Zhao Z, Yang J, Buchan A. Prolonged but delayed postischemic hypothermia: a long term outcome study in the rat middle cerebral artery occlusion model. J Cereb Blood Flow Metab. 2000; 20(12):1702. PubMed PMID: 4814.

17. Corbett D, Hamilton M, Colbourne F. Persistent neuroprotection with prolonged postischemic hypothermia in adult rats subjected to transient middle cerebral artery occlusion. Exp Neurol. 2000 May; 163(1):200-6. PubMed PMID: 10785459.

18. Colbourne F, Corbett D. Delayed Postischemic Hypothermia: A six month survival study using behavioral and histological assessments of neuroprotection. J Neurosci. 1995; 15:7250. PubMed PMID: 2685.

19. Xing C, Wang X, Cheng C, Montaner J, Mandeville E, Leung W, et al. Neuronal production of lipocalin-2 as a help-me signal for glial activation. Stroke. 2014 July; 45(7):2085-92. PubMed PMID: 24916903. Pubmed Central PMCID: 4122238.

20. Rajput P S, Lyden P D, Chen B, Lamb J A, Pereira B, Lamb A, et al. Protease activated receptor-1 mediates cytotoxicity during ischemia using in vivo and in vitro models. Neuroscience. 2014 Sep. 28; 281C:229-40. PubMed PMID: 25261684.

21. Wang D, Zhao Y, Zhang Y, Zhang T, Shang X, Wang J, et al. Hypothermia protects against oxygen-glucose deprivation-induced neuronal injury by down-regulating the reverse transport of glutamate by astrocytes as mediated by neurons. Neuroscience. 2013 May 1; 237:130-8. PubMed PMID: 23402854.

22. Jha M K, Seo M, Kim J H, Kim B G, Cho J Y, Suk K. The secretome signature of reactive glial cells and its pathological implications. Biochim Biophys Acta. 2013 November; 1834(11):2418-28. PubMed PMID: 23269363.

23. Allaman I, Belanger M, Magistretti P J. Astrocyte-neuron metabolic relationships: for better and for worse. Trends Neurosci. 2011 February; 34(2):76-87. PubMed PMID: 21236501. Epub 2011/01/18. eng.

24. Barreto G, White R E, Ouyang Y, Xu L, Giffard R G. Astrocytes: targets for neuroprotection in stroke. Cent Nery Syst Agents Med Chem. 2011 Jun. 1; 11(2):164-73. PubMed PMID: 21521168. Pubmed Central PMCID: 3167939.

25. Du F, Wu X M, Gong Q, He X, Ke Y. Hyperthermia conditioned astrocyte-cultured medium protects neurons from ischemic injury by the up-regulation of HIF-1 alpha and the increased anti-apoptotic ability. Eur J Pharmacol. 2011 September; 666(1-3):19-25. PubMed PMID: 21620821.

26. Haskew-Layton R E, Payappilly J B, Smirnova N A, Ma T C, Chan K K, Murphy T H, et al. Controlled enzymatic production of astrocytic hydrogen peroxide protects neurons from oxidative stress via an Nrf2-independent pathway. Proc Natl Acad Sci USA. 2010 Oct. 5; 107(40): 17385-90. PubMed PMID: 20855618. Pubmed Central PMCID: 2951414.

27. Lin C H, Cheng F C, Lu Y Z, Chu L F, Wang C H, Hsueh C M. Protection of ischemic brain cells is dependent on astrocyte-derived growth factors and their receptors. Exp Neurol. 2006 September; 201(1):225-33. PubMed PMID: 16765947.

28. Trendelenburg G, Dirnagl U. Neuroprotective role of astrocytes in cerebral ischemia: focus on ischemic preconditioning. Glia. 2005 June; 50(4):307-20. PubMed PMID: 15846804.

29. del Zoppo G J. The neurovascular unit in the setting of stroke. J Intern Med. 2010 February; 267(2):156-71. PubMed PMID: 20175864. Pubmed Central PMCID: 3001328. Epub 2010/02/24. eng.

30. Chen B, Friedman B, Whitney M A, Winkle J A, Lei I F, Olson E S, et al. Thrombin activity associated with neuronal damage during acute focal ischemia. J Neurosci. 2012 May 30; 32(22):7622-31. PubMed PMID: 22649241. Pubmed Central PMCID: 3383068. Epub 2012/06/01. eng.

31. Chen B, Friedman B, Cheng Q, Tsai P, Schim E, Kleinfeld D, et al. Severe blood-brain barrier disruption and surrounding tissue injury. Stroke. 2009 December; 40(12):e666-74. PubMed PMID: 19893002. Pubmed Central PMCID: 2819286. Epub 2009/11/07. eng.

32. Antonic A, Dottori M, Leung J, Sidon K, Batchelor P E, Wilson W, et al. Hypothermia protects human neurons. Int J Stroke. 2014 July; 9(5):544-52. PubMed PMID: 24393199.

33. Clark D L, Penner M, Orellana-Jordan I M, Colbourne F. Comparison of 12, 24 and 48 h of systemic hypothermia on outcome after permanent focal ischemia in rat. Exp Neurol. 2008 August; 212(2):386-92. PubMed PMID: 18538766.

34. Maier C M, Ahern Kv, Cheng M L, Lee J E, Yenari M A, Steinberg G K, et al. Optimal Depth and Duration of Mild Hypothermia in a Focal Model of Transient Cerebral Ischemia: Effects on Neurologic Outcome, Infarct Size, Apoptosis, and Inflammation•Editorial Comment: Effects on Neurologic Outcome, Infarct Size, Apoptosis, and Inflammation. Stroke. 1998 Oct. 1, 1998; 29(10):2171-80.

35. Carroll M, Beek O. Protection Against Hippocampal CA1 Cell Loss by Post-Ischemic Hypothermia is Dependent on Delay of Initiation and Duration. Metabolic Brain Disease. 1992; 7(1):45. PubMed PMID: 4811.

36. Jackson-Friedman C, Lyden P D, Nunez S, Jin A, Zweifler R. High dose baclofen is neuroprotective but also causes intracerebral hemorrhage: A quantal bioassay study using the intraluminal suture occlusion method. ExpNeurol. 1997; 147:346. PubMed PMID: 2781.

37. Lyden P, Pereira B, Chen B, Zhao L, Lamb J, Lei I F, et al. Direct thrombin inhibitor argatroban reduces stroke damage in 2 different models. Stroke. 2014 March; 45(3): 896-9. PubMed PMID: 24473182. Pubmed Central PMCID: 3995814.

38. Lyden P, Lonzo L, Nunez S. Combination chemotherapy extends the therapeutic window to 60 minutes after stroke. J Neurotrauma. 1995 April; 12(2):223-30. PubMed PMID: 7629868. Epub 1995/04/01. eng.

39. Zhang H T, Xue J H, Zhang Z W, Kong H B, Liu A J, Li S C, et al. Cold-inducible RNA-binding protein inhibits neuron apoptosis through the suppression of mitochondrial apoptosis. Brain Res. 2015 Oct. 5; 1622:474-83. PubMed PMID: 26168889.

40. Liu J, Xue J, Zhang H, Li S, Liu Y, Xu D, et al. Cloning, expression, and purification of cold inducible RNA-binding protein and its neuroprotective mechanism of action. Brain Res. 2015 Feb. 9; 1597:189-95. PubMed PMID: 25498861.

41. Jackson T C, Manole M D, Kotermanski S E, Jackson E K, Clark R S, Kochanek P M. Cold stress protein RBM3 responds to temperature change in an ultra-sensitive manner in young neurons. Neuroscience. 2015 Oct. 1; 305: 268-78. PubMed PMID: 26265550. Pubmed Central PMCID: 4570027.

42. Peretti D, Bastide A, Radford H, Verity N, Molloy C, Martin M G, et al. RBM3 mediates structural plasticity and protective effects of cooling in neurodegeneration. Nature. 2015 Feb. 12; 518(7538):236-9. PubMed PMID: 25607368. Pubmed Central PMCID: 4338605.
43. Thieringer H A, Jones P G, Inouye M. Cold shock and adaptation. Bioessays. 1998 January; 20(1):49-57. PubMed PMID: 9504047.
44. Parker S J, Raedschelders K, Van Eyk J E. Emerging proteomic technologies for elucidating context-dependent cellular signaling events: A big challenge of tiny proportions. Proteomics. 2015 May; 15(9):1486-502. PubMed PMID: 25545106.
45. Ge Y, Van Eyk J. Cardiovascular disease: the leap towards translational and clinical proteomics. Proteomics Clinical applications. 2014 August; 8(7-8):473-5. PubMed PMID: 25123748.
46. Gundry R L, White M Y, Murray C I, Kane L A, Fu Q, Stanley B A, et al. Preparation of proteins and peptides for mass spectrometry analysis in a bottom-up proteomics workflow. Current protocols in molecular biology/edited by Frederick M Ausubel [et al]. 2009 October; Chapter 10:Unit10 25. PubMed PMID: 19816929. Pubmed Central PMCID: 2905857.
47. Stanley B A, Gundry R L, Cotter R J, Van Eyk J E. Heart disease, clinical proteomics and mass spectrometry. Disease markers. 2004; 20(3):167-78. PubMed PMID: 15502250. Pubmed Central PMCID: 3839266.
48. Van Winkle J A, Chen B, Lei I F, Pereira B, Rajput P S, Lyden P D. Concurrent middle cerebral artery occlusion and intra-arterial drug infusion via ipsilateral common carotid artery catheter in the rat. J Neurosci Methods. 2012 Dec. 20; 213(1):63-9. PubMed PMID: 23261656. Epub 2012/12/25. Eng.
49. Saver J L, Goyal M, Diener H C, Investigators SP. Stent-Retriever Thrombectomy for Stroke. N Engl J Med. 2015 Sep. 10; 373(11):1077. PubMed PMID: 26352820.
50. Campbell B C, Mitchell P J, Kleinig T J, Dewey H M, Churilov L, Yassi N, et al. Endovascular therapy for ischemic stroke with perfusion-imaging selection. N Engl J Med. 2015 Mar. 12; 372(11):1009-18. PubMed PMID: 25671797.
51. Goyal M, Demchuk A M, Menon B K, Eesa M, Rempel J L, Thornton J, et al. Randomized assessment of rapid endovascular treatment of ischemic stroke. N Engl J Med. 2015 Mar. 12; 372(11):1019-30. PubMed PMID: 25671798.
52. Berkhemer O A, Fransen P S, Beumer D, van den Berg L A, Lingsma H F, Yoo A J, et al. A randomized trial of intraarterial treatment for acute ischemic stroke. N Engl J Med. 2015 Jan. 1; 372(1):11-20. PubMed PMID: 25517348.
53. Lyden P, Jackson-Friedman C, Shin C, Hassid S. Synergistic combinatorial stroke therapy: A quantal bioassay of a GABA agonist and a glutamate antagonist. Experimental Neurology. 2000; 163:477. PubMed PMID: 4546.
54. O'Collins V E, Macleod M R, Cox S F, Van Raay L, Aleksoska E, Donnan G A, et al. Preclinical drug evaluation for combination therapy in acute stroke using systematic review, meta-analysis, and subsequent experimental testing. J Cereb Blood Flow Metab. 2011 March; 31(3):962-75. PubMed PMID: 20978519. Pubmed Central PMCID: 3063631. Epub 2010/10/28. eng.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method of treating, preventing, reducing the likelihood of having, reducing the severity of and/or slowing the progression of a condition in a subject in need thereof, wherein a body part of the subject has been affected by the condition for a time period T0, comprising:
   (a) reperfusing the affected body part for a time period TR;
   (b) implementing a first temperature transition C0 by changing a temperature of the subject's body and/or the affected body part to a first target temperature of about 27-33° C., and maintaining the temperature of the subject's body and/or the affected body part at the first target temperature for a time period of T1;
   (c) implementing a second temperature transition C1 by changing the temperature of the subject's body and/or the affected body part to a second target temperature, and maintaining the temperature of the subject's body and/or the affected body part at the second target temperature for a time period of T2; and
   (d) implementing a third temperature transition C2 by changing the temperature of the subject's body and/or the affected body part to a third target temperature, and maintaining the temperature of the subject's body and/or the affected body part at the third target temperature for a time period of T3,
   thereby treating, preventing, reducing the likelihood of having, reducing the severity of and/or slowing the progression of the condition in the subject,
   wherein $(T1+T2)=xT0+yTR$, wherein x and y are integers, or
   wherein $fT1+(1-f)T2=xT0+yTR$, wherein x and y are integers and f is 0-1 or a fraction therebetween.

2. The method of claim 1, wherein the first target temperature is about 30, 31, 32, or 33° C.

3. The method of claim 1, wherein C0 is accomplished within about 1-5, 5-10, 10-15, 15-20, 20-25, or 25-30 minutes.

4. The method of claim 1, wherein the second target temperature is about 34, 35, or 36° C.

5. The method of claim 1, wherein C1 is accomplished within about 1-5, 5-10, 10-15, 15-20, 20-25, or 25-30 minutes.

6. The method of claim 1, wherein the third target temperature is about or 38° C.

7. The method of claim 1, wherein C2 is accomplished within about 1-5, 5-10, 10-15, 15-20, 20-25, or 25-30 minutes.

8. The method of claim 1, wherein the first target temperature is about 33° C., the second target temperature is about 35° C., and the third target temperature is about 37° C.

9. The method of claim 1, wherein $(T1+T2)=xT0+yTR$, wherein x is 1, 2, 3, 4, or 5, and y is 1, 2, 3, 4 or 5.

10. The method of claim 1, wherein $fT1+(1-f)T2=xT0+yTR$, wherein x is 1, 2, 3, 4, or 5 and y is 1, 2, 3, 4, or 5 and f is 0, $\frac{1}{2}$, $\frac{1}{3}$, $\frac{2}{3}$, $\frac{1}{4}$, $\frac{3}{4}$, $\frac{1}{5}$, $\frac{2}{5}$, $\frac{3}{5}$, $\frac{4}{5}$, $\frac{1}{6}$, $\frac{5}{6}$, $\frac{1}{7}$, $\frac{2}{7}$, $\frac{3}{7}$, $\frac{4}{7}$, $\frac{5}{7}$, $\frac{6}{7}$, $\frac{1}{8}$, $\frac{3}{8}$, $\frac{5}{8}$, $\frac{7}{8}$, $\frac{1}{9}$, $\frac{2}{9}$, $\frac{3}{9}$, $\frac{4}{9}$, $\frac{5}{9}$, $\frac{6}{9}$, $\frac{7}{9}$, $\frac{8}{9}$, $\frac{1}{10}$, $\frac{3}{10}$, $\frac{7}{10}$, $\frac{9}{10}$, or 1.

11. The method of claim 1, further comprising:
   (e) implementing a fourth temperature transition C3 by changing the temperature of the subject's body and/or the affected body part to a fourth target temperature, and maintaining the temperature of the subject's body and/or the affected body part at the fourth target temperature for a time period of T4.

12. The method of claim 11, further comprising:
   (f) implementing a fifth temperature transition C4 by changing the temperature of the subject's body and/or the affected body part to a fifth target temperature, and maintaining the temperature of the subject's body and/or the affected body part at the fifth target temperature for a time period of T5.

13. The method of claim 1, wherein the condition is hypoxemia, hypoxia, ischemia, myocardial ischemia, cerebral ischemia, cardiac arrest, stroke, ischemic stroke, hemorrhagic stroke, transient ischemic attack, traumatic brain injury, traumatic spinal cord injury, hypoxic-ischemic injury, or hypoxic-ischemic encephalopathy, perinatal asphyxia, or a combination thereof.

14. A system, comprising:
   a temperature management module configured for changing and/or maintaining a temperature of a subject's body and/or body part; and
   a computer configured for operating the temperature management module to change and/or maintain the temperature of the subject's body and/or body part, wherein the computer comprises
   a memory configured for storing one or more programs; and
   one and more processors configured for executing the one or more programs, wherein the one or more programs comprise
   instructions for operating the system and/or modules thereof to change and/or maintain a temperature of a subject's body and/or body part, and to control the temperature of the subject's body and/or body part in accordance with the method of claim 1.

15. The system of claim 14, wherein the temperature management module comprises a cooling catheter, cooling blanket, ice pack, iced lavage, transnasal cooling cannula, cooling helmet, cooling cap, cooling wrap, gel pad, or extracorporeal blood cooling machine, or a combination thereof.

16. A computer, comprising:
    a memory configured for storing one or more programs; and
    one and more processors configured for executing the one or more programs,
    wherein the one or more programs comprise instructions for operating a temperature management module configured to change and/or maintain a temperature of a subject's body and/or body part, and to control the temperature of the subject's body and/or body part in accordance with the method of claim 1.

17. A computer implemented method of treating, preventing, reducing the likelihood of having, reducing the severity of and/or slowing the progression of a condition in a subject, comprising:
    providing the computer of claim 16;
    connecting the computer to a temperature management module configured for changing and/or maintaining a temperature of a subject's body and/or body part to control the temperature of the subject's body and/or body part, and to detect biomarkers in the subject's body and/or body part; and
    operating the computer to operate the temperature management module to change and/or maintain the temperature of the subject's body and/or body part, to control the temperature of the subject's body and/or body part, and to detect biomarkers in the subject's body and/or body part, thereby treating, preventing, reducing the likelihood of having, reducing the severity of and/or slowing the progression of the condition in the subject.

18. A method of treating, preventing, reducing the likelihood of having, reducing the severity of and/or slowing the progression of a condition in a subject, wherein a body part of the subject has been affected by the condition for a time period T0 and then reperfused for a time period TR, comprising:
    (a) implementing a first temperature transition C0 by changing a temperature of the subject's body and/or the affected body part to a first target temperature of about 27-33° C., and maintaining the temperature of the subject's body and/or the affected body part at the first target temperature for a time period of T1;
    (b) implementing a second temperature transition C1 by changing the temperature of the subject's body and/or the affected body part to a second target temperature, and maintaining the temperature of the subject's body and/or the affected body part at the second target temperature for a time period of T2; and
    (c) implementing a third temperature transition C2 by changing the temperature of the subject's body and/or the affected body part to a third target temperature, and maintaining the temperature of the subject's body and/or the affected body part at the third target temperature for a time period of T3,
    thereby treating, preventing, reducing the likelihood of having, reducing the severity of and/or slowing the progression of the condition in the subject,
    wherein $(T1+T2)=xT0+yTR$, wherein x and y are integers or
    wherein $fT1+(1-f)T2=xT0+yTR$, wherein x and y are integers and f is 0-1 or a fraction therebetween.

\* \* \* \* \*